(12) United States Patent
Morris et al.

(10) Patent No.: US 8,487,167 B2
(45) Date of Patent: Jul. 16, 2013

(54) NON-TRANSGENIC SOFT TEXTURED TETRAPLOID WHEAT PLANTS HAVING GRAIN WITH SOFT TEXTURED ENDOSPERM, ENDOSPERM THEREFROM AND USES THEREOF

(75) Inventors: Craig F. Morris, Pullman, WA (US); Leonard R. Joppa, Fargo, ND (US); Marco C. Simeone, Viterbo (IT); Domenico Lafiandra, Montefiascone (IT)

(73) Assignee: The United States of America, as represented by the Secretary of Agriculture, Washington, DC (US)

( * ) Notice: Subject to any disclaimer, the term of this patent is extended or adjusted under 35 U.S.C. 154(b) by 404 days.

(21) Appl. No.: 12/538,858

(22) Filed: Aug. 10, 2009

(65) Prior Publication Data
US 2011/0033605 A1 Feb. 10, 2011

(51) Int. Cl.
A01H 4/00 (2006.01)
A01H 5/00 (2006.01)
A01H 5/10 (2006.01)
A21D 2/00 (2006.01)

(52) U.S. Cl.
USPC .................. 800/320.3; 435/410; 426/622

(58) Field of Classification Search
None
See application file for complete search history.

(56) References Cited

U.S. PATENT DOCUMENTS
7,598,443 B2 * 10/2009 Edge et al. ................. 800/320.3

OTHER PUBLICATIONS

Gazza et al. Development of durum wheat (*Triticum turgidum* ssp durum) lines with soft kernel texture by chromosome engineering. pp. 339-341 in R. Appels, R. et al. (editors) Proceedings of the 11th International Wheat Genetics Symposium Aug. 24-29, 2008, Brisbane, QLD, Australia, vol. 2. Syndney University Press, Sydney.*
Giroux et al. Wheat grain hardness results from highly conserved mutations in the friabilin components puroindoline a and b. Proc Natl Acad Sci U S A. May 26, 1998;95(11):6262-6.*

* cited by examiner

*Primary Examiner* — Cynthia Collins
(74) *Attorney, Agent, or Firm* — Elizabeth R. Sampson; John D. Fado; Lesley Shaw

(57) ABSTRACT

The present invention relates to non-transgenic tetraploid wheat plants having soft textured endosperm, methods for constructing said non-transgenic plants using cytogenetics and classical breeding techniques, endosperm therefrom and uses thereof.

18 Claims, 33 Drawing Sheets

NON-TRANSGENIC SOFT TEXTURED TETRAPLOID WHEAT PLANTS HAVING GRAIN WITH SOFT TEXTURED ENDOSPERM, ENDOSPERM THEREFROM AND USES THEREOF

FIELD OF THE INVENTION

The invention relates to wheat breeding, new non-transgenic tetraploid wheat cultivars having grain with soft textured endosperm, methods of producing the new non-transgenic tetraploid wheat cultivars and uses thereof.

BACKGROUND OF THE INVENTION

Wheat is one of the most important food crops in the world, and is a dominant grain of world commerce. As is well known in the art, the hardness of wheat grain varies between different wheat cultivars. Grain hardness refers to the texture of the kernel (caryopsis), in particular whether the endosperm is physically hard or soft. Grain texture, or "hardness", influences processing, including e.g., milling, the characteristics of milled granular products of different wheat grain varieties, and how those varieties and granular products are used in foods.

Different grain textures are exploited to produce a wide variety of granular products including e.g., flours, semolinas, farinas, as well as a wide variety of food products. Generally speaking, hard wheat (*Triticum aestivum*) is used for bread and pasta, whereas soft wheat (*T. aestivum*) is used for cookies, cakes and pastries (Morris & Rose, Cereal Grain Quality, Chapman & Hall, New York, N.Y., pp. 3-54 (1996)). Typically, the very hard durum wheat (*T. turgidum* ssp. *durum*) is used in pasta, bread, couscous and bulgur.

Soft wheat typically produces a finer granulation upon milling or grinding, hard wheat a coarser granulation, and durum wheat a very coarse granulation. Although granulation is controlled somewhat by the art of milling, it is still highly limited by the inherent hardness characteristics of the wheat variety.

Durum wheat is universally recognized as the ideal raw material for the production of quality pasta products. In particular, durum wheat is high in protein and gluten, both of which are necessary components for pasta making. As noted above, durum wheat typically has a grain with a very hard textured endosperm. Consequently, it is typically milled into a granular meal of coarse particle size called semolina. Finer granulations can be produced however to produce a durum meal or flour of a particular granularity, more energy is required for milling than is required for the milling of other wheat having grain with softer textured endosperm. Thus, it is particularly difficult to obtain a finely granulated flour from durum wheat without incurring excessive starch damage and expending considerable energy. Yet, finer granulations are increasingly preferred by modern pasta manufacturers.

Starch damage influences water absorption and other dough properties, and despite other desirable factors e.g., protein content, pasta prepared with highly damaged starch is typically of inferior quality e.g., is sticky and has poor "mouth feel", and is therefore considered by most people to be unacceptable. See e.g., Pasta and Noodle Technology James E. Kruger et al. eds., *American Association of Cereal Chemists* (1996).

Thus, the energy expended in milling the durum wheat kernels into semolina and flour must be carefully controlled so as to achieve the desired granulation with minimal starch damage. Therefore, to take full advantage of the beneficial and desirable characteristics of durum wheat, what is needed in the art is a durum wheat having grain with soft textured endosperm. Indeed, such a wheat cultivar would inter alia, produce soft textured wheat grain which could be ground into various granulations including finely textured flour without extensive amounts of starch damage an/or which could be ground more easily into semolina with much less energy expended.

Transgenic soft kernel wheat is known (see e.g., U.S. Pat. No. 6,596,930). However, there are barriers to widespread use of genetically modified cultivars. Indeed, genetically modified crops face high regulatory and research costs, and are opposed by many NGOs, and several governments, particularly within the European Community and Japan.

Therefore, a durum wheat having grain with soft textured endosperm that is also non-transgenic would meet the need for soft textured durum, and would also get around the barriers to widespread use that face genetically modified crops.

Fortunately, as will be clear from the following disclosure, the present invention provides for these and other needs.

SUMMARY OF THE INVENTION

One exemplary embodiment of the invention provides a non-transgenic tetraploid wheat plant having grain with soft textured endosperm wherein the non-transgenic tetraploid wheat plant having grain with soft textured endosperm has functional Ph1 and diploid like behavior in meosis. In one exemplary embodiment, the non-transgenic tetraploid wheat plant is a durum wheat plant. In another exemplary embodiment, the non-transgenic tetraploid wheat plant is capable of serving as a parent in a genetic cross.

Another exemplary embodiment of the invention provides a seed of a non-transgenic tetraploid wheat plant having grain with soft textured endosperm, wherein the seed produces a tetraploid wheat plant having grain with soft textured endosperm. In another exemplary embodiment, the invention provides a non-transgenic tetraploid wheat plant having grain with soft textured endosperm, or a part thereof, produced by growing the seed.

Another exemplary embodiment of the invention provides a tissue culture of regenerable cells produced from a non-transgenic tetraploid wheat plant having grain with soft textured endosperm. In another exemplary embodiment, the invention provides a protoplast produced from the tissue culture a tissue culture of regenerable cells produced from a non-transgenic tetraploid wheat plant having grain with soft textured endosperm.

Another exemplary embodiment of the invention provides a non-transgenic tetraploid wheat plant having grain with soft textured endosperm, or a part thereof, having all the physiological and morphological characteristics of the variety Soft Svevo durum wheat WAS 080240001 (hereinafter, Soft Svevo), representative seed of such line having been deposited under ATCC Accession No. PTA-10087. In one exemplary embodiment, the non-transgenic tetraploid wheat plant is capable of serving as a parent in a genetic cross. In another exemplary embodiment, a seed of the non-transgenic tetraploid wheat plant produces a non-transgenic tetraploid wheat plant having grain with soft textured endosperm. In another exemplary embodiments the non-transgenic tetraploid wheat plant is used to produce a tissue culture of regenerable cells. In another exemplary embodiment a protoplast is produced from the tissue culture of regenerable cells. In still another exemplary embodiment, the invention provides a non-transgenic tetraploid wheat plant having grain with soft textured endosperm, regenerated from the tissue culture of regenerable cells produced from a non-transgenic tetraploid wheat plant having grain with soft textured endosperm.

Another exemplary embodiment of the invention provides a hybrid wheat plant, wherein the lineage of at least one parent plant comprises a non-transgenic tetraploid wheat plant having grain with soft textured endosperm, having all the physiological and morphological characteristics of the variety Soft Svevo, representative seed of such line having been deposited under ATCC Accession No. PTA-10087. In one exemplary embodiment the at least one parent plant of the hybrid wheat plant is the non-transgenic tetraploid wheat plant having grain with soft textured endosperm, with all the physiological and morphological characteristics of the variety Soft Svevo, representative seed of such line having been deposited under ATCC Accession No. PTA-10087.

Another exemplary embodiment of the invention provides a non-transgenic tetraploid wheat plant having grain with soft textured endosperm having ATCC Accession No. PTA-10087 or a selfed progeny thereof or an F1 hybrid thereof wherein the non-transgenic tetraploid wheat plant has grain with soft textured endosperm.

Another exemplary embodiment of the invention provides a semolina flour comprising soft textured endosperm from a non-transgenic tetraploid wheat plant having grain with soft textured endosperm. In one exemplary embodiment, the semolina flour of is made from a non-transgenic tetraploid wheat plant having ATCC Accession No. PTA-10087 or a progeny thereof.

Other features, objects and advantages of the invention will be apparent from the detailed description which follows.

DETAILED DESCRIPTION OF THE INVENTION

Definitions

Figure 1:
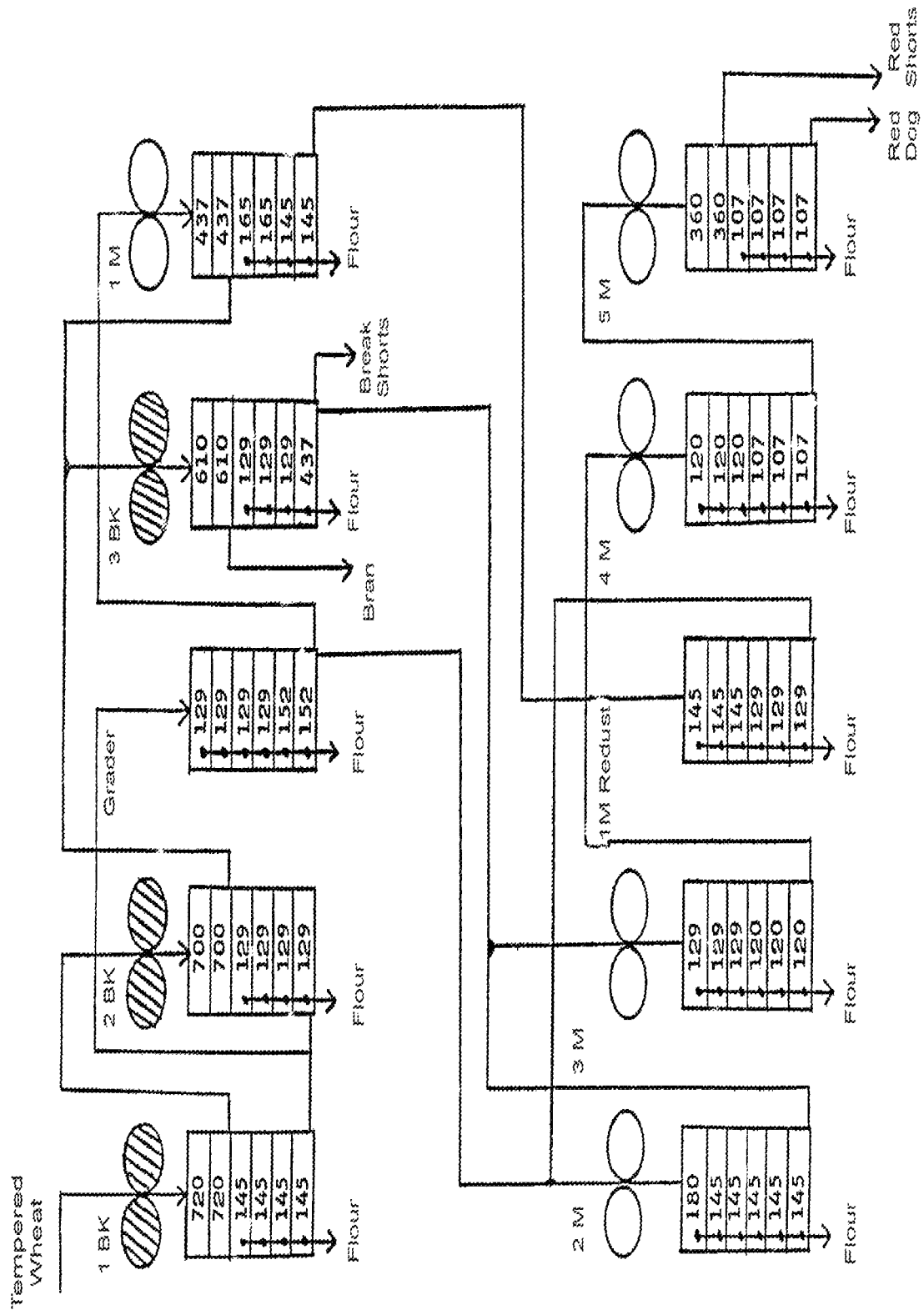
FIG. 1. Miag Multomat flour mill schematic flow diagram.

The term "plant" as used herein refers to whole plants, plant bodies, plant organs (e.g., leaves, stems, flowers, roots, etc.), seeds, plant tissues, plant cells and progeny of same. In an exemplary embodiment, a plant cell includes callus. In another exemplary embodiment, a plant organ includes a root, a leaf, a flower and/or the like. The term "plant" refers to plants of any variety of ploidy levels, including polyploid, diploid, haploid and hemizygous.

The term "transgenic plant" as used herein refers to a plant comprising a heterologous nucleic acid sequence that codes for or otherwise influences expression of the desirable trait of soft kernel texture wherein the heterologous nucleic acid sequence was introduced into the plant, at some point in its lineage, by genetic engineering techniques. Thus, the term "transgenic plant" refers to tetraploid wheat plants which are the direct result of transformation with a heterologous nucleic acid or transgene, and the progeny and descendants of transformed plants which comprise the introduced heterologous nucleic acid or transgene. In an exemplary embodiment, a "transgenic plant" is a tetraploid wheat plant having grain with soft kernel texture wherein the soft kernel texture is a result of expression of a heterologous transgene e.g., puroindoline a and/or puroindoline b, that codes for and/or influences the expression of soft kernel texture.

A "non-transgenic tetraploid wheat plant having grain with soft kernel texture" or a "non-transgenic durum wheat plant having grain with soft kernel texture" as used herein, refers to a tetraploid wheat plant that does not comprise heterologous nucleic acid sequences for the desirable trait of soft kernel texture, either as a direct result of transformation with a heterologous nucleic acid or transgene, or as a result of inheritance as the progeny and descendants of transformed plants which comprise the introduced heterologous nucleic acid or transgene. Typically, the desirable traits of a "non-transgenic tetraploid wheat plant having grain with soft kernel texture" e.g., soft kernel texture, are produced and transmitted from one generation to the next by virtue of classical selective breeding techniques without the need for any genetic engineering techniques. Thus, a "non-transgenic tetraploid wheat plant having grain with soft kernel texture" is a wheat plant that is non-transgenic for genes and/or at loci that code for or otherwise influence the desirable soft kernel texture trait. Thus, in an exemplary embodiment, a non-transgenic tetraploid wheat plant having grain with soft kernel texture is non-transgenic at the puroindoline a and puroindoline b loci. However, in some exemplary embodiments, a non-transgenic tetraploid wheat plant having grain with soft kernel texture is transgenic at loci that do not directly code for and/or influence the desirable soft kernel trait. Thus, in one exemplary embodiment, a non-transgenic tetraploid wheat plant having grain with soft kernel texture is non-transgenic at the puroindoline a and puroindoline b loci, but is transgenic for another trait, e.g., herbicide resistance.

The expression "heterologous nucleic acid sequence" or "heterologous gene" as used herein, refers to a gene that is not in its natural environment (in other words, has been altered by the hand of man). In an exemplary embodiment, a heterologous gene is a gene from one species that is introduced into another species. In another exemplary embodiment, a "heterologous gene" or a "heterologous nucleic acid sequence" is a nucleic acid sequence joined to a regulatory element(s) e.g., a promoter, that is not found naturally associated with the "heterologous gene" or "heterologous nucleic acid sequence".

The term "tetraploid wheat plant" as used herein, refers to a wheat plant having two sets of paired chromosomes, or four times the haploid number of individual chromosomes. The haploid number of wheat chromosomes is seven. Thus, a diploid wheat plant has seven pairs of chromosomes or 14 chromosomes in total. A "tetraploid wheat plant" has two sets of seven pairs, or 28 chromosomes total. Similarly, a "hexaploid wheat plant" has six pairs of seven chromosomes, or 42 chromosomes total. In an exemplary embodiment, a tetraploid wheat plant is a durum wheat plant.

The expression "having functional Ph1 and diploid like behavior in meiosis" as used herein, refers to a wheat plant that exhibits activity of Ph1 (Pairing homoeologous 1) locus as evidenced by the suppression of pairing among and between homoeologous chromosomes in polyploid wheat, while allowing the normal pairing of homologous chromosomes. Because of Ph1 activity, polyploid wheats behave as functional diploids in their controlled and orderly pairing at meiosis. Diploid-like behavior in meiosis refers to the stable transmission of genetic traits in typical Mendelian genetic ratios, e.g., 1:2:1 segregation of a single gene trait in the F1 generation of a cross between two diploid parents.

The term "soft textured endosperm" "soft textured grain", "grain with soft textured endosperm" "soft grain" "soft kernel" "soft kernel texture" or any gramatically equivalent expression as used herein, refers to grain kernels from a non-transgenic tetraploid wheat plant that have a hardness index of between about 10 to about 45 as measured by the Perten SKCS 4100 (Perten Instruments, Reno, Nev. See e.g., Instruction Manual, Single-Kernel Characterization System, Model SKCS 4100; Perten Instruments, Inc.: 6444 South Sixth Street Road, Springfield, Ill. 62707) or by equivalent technology. Kernel hardness is typically expressed as an index/value of –20 to 120.

The kernel hardness associated with grain of hard wheats e.g., hard durum wheats, typically have SKCS values from about 60 to about 100. However, in some exemplary embodiments, the kernel hardness associated with grain of hard wheats have SKCS values in a range that is from about 50 to about 110. In other exemplary embodiments, the kernel hardness associated with grain of hard wheats have an SKCS hardness value in a range that is from about 70 to about 85.

In contrast, the kernel hardness associated with grain of soft wheats e.g., soft durum and soft *T. aestivum* typically have SKCS hardness values in a range that is from about 10 to about 45. However, in some exemplary embodiments, the kernel hardness associated with grain of soft wheats have SKCS hardness values in a range that is from about 0 to about 55. In other exemplary embodiments, the kernel hardness associated with grain of soft wheats have SKCS hardness values in a range that is from about 15 to about 35. Thus, in an exemplary embodiment, the grain of a non-transgenic tetraploid wheat plant having soft textured endosperm has a hardness value that is in a range that is between about 10 to about 45. In another exemplary embodiment, the grain of a non-transgenic tetraploid wheat plant having soft textured endosperm has a hardness value that is in a range that is between about 15 to about 35 as measured by the Perten SKCS 4100. And, in still another exemplary embodiment, the grain of a non-transgenic tetraploid wheat plant having soft textured endosperm has a hardness value that is in a range that is between about 0 to about 55 as measured by the Perten SKCS 4100.

The term "starch damage" as used herein, refers to mechanical damage that afflicts starch granules as a result of milling. Typically, starch damage is manifest as cracks and breaks in the starch granule, and can be quantitated by any method known in the art (see below).

The term "cross" or "crossing" as used herein refers to a simple X by Y cross, or the process of backcrossing, depending on the context.

The term "backcross" as used herein refers to a process in which a breeder crosses a hybrid progeny line back to one of the parental genotypes one or more times.

The terms "disomic", "ditelosomic", "heterozygote", "substitution line", "filial", "homoeologous", "bivalent", "monosomic", "monovalent", "ring bivalent", "test cross", "translocation", "trivalent", "double ditelosomic", "telosomic", "telomeric", "nullisomic", "tetrasomic" or the plural or adjective form of any of these as used herein have meanings typically ascribed in the art (see e.g., Rieger R., Michaelis A., Green M. M. (1976) Glosary of Genetics and Cytogenetics. Classical and Molecular, 4th ed., Springer-Verlag, Berlin; Gill B. S. (1986) *A proposal for wheat chromosome band nomenclature*. In: North American Wheat Genetic Mapping and Cytogenetic Stocks Workshop, Apr. 17-19, 1986, University of Missouri, Columbia. Ed: Qualset CO and McGuire PE. The National Association of Wheat Growers Foundation, Washington, D.C. 11-15; Gill B. S., et al. (1991) Genome 34:830-839; Kimber G and Sears ER (1968) Nomenclature for the description of aneuploids in the Triticinae. In: Proc 3rd Int Wheat Genet Symp, Ed: Findlay K W and Shepherd K W. Can berra, Australia. 468-473; and Raupp W. J., Friebe B., Gill B. S. *Suggested guidelines for the nomenclature and abbreviation of the genetic stocks of wheat and its relatives*, http://wheat.pw.usda.gov/ggpages/nomenclature.html.

Pedigrees follow the convention of Purdy L. H., Loegering W. Q., Konzak C. F. et al. (1968) *Crop Science* 8:405-406.

The abbreviations "F1", "BC1" and higher numerical values of each alone and in combination (e.g. "BC1F1") represent "first filial generation", "first back cross generation", respectively, etc.

The term "durum flour" as used herein has meaning commonly used in the art and as set forth in CFR §137.220. The expression "Whole durum flour" as used herein has meaning commonly used in the art and as set forth in CFR §137.225 The term "Semolina' as used herein has meaning commonly used in the art and as set forth in CFR §137.320, and further restrictions relative to the definitions as regards measuring granulation, ash content, etc. are as provided by current statute.

Taxonomic classifications follow those of M. W. van Slageren, *Wild wheats: a monograph of Aegilops L. and Amblyopurum (Jaub. & Spach) Eig (Poaceae)* (1994), Agricultural University, Wageningen, the Netherlands.

Milling terms are well-known to those of skill in the art and can be found e.g., in: Posner E. S., Hibbs, A. N. (1997) *Wheat Flour Milling* American Association of Cereal Chemists, St. Paul, Minn.

I. Introduction

In an exemplary embodiment, the invention provides a non-transgenic tetraploid wheat plant having grain with soft kernel texture (soft-textured endosperm). In another exemplary embodiment, the invention provides non-transgenic tetraploid wheat plants having grain with soft-textured endosperm, which have a functinal Ph1 and diploid like behavior in meiosis and which therefore are able to serve as a parent in a genetic cross. In still other exemplary embodiments the invention provides milled products from the disclosed non-transgenic tetraploid wheat plants having grain with soft kernel texture. Thus, in addition to providing a non-transgenic tetraploid wheat plant having grain with soft kernel texture the invention provides non-transgenic tetraploid wheat plants that are useful as foundation stock for the production of new wheat varieties, and provided milled products derived from the soft textured endosperm produced by the non-transgenic tetraploid wheat plants having grain with soft kernel texture.

Variations in the characteristics and quality of wheat grain influence how successfully wheat and flour and other granular products perform in consumer products. Enhancing wheat quality improves processing efficiencies, makes more desirable and more diverse consumer products and thus ensures the competitiveness of farmers, grain merchandisers, millers, and end processors. The efficient and innovative use of wheat grain depends on both controlling and exploiting variation in its basic quality traits.

One basic quality trait of importance is kernel texture. Indeed, different wheat grain textures are exploited to produce the wide variety of granular products e.g., flours, semolinas, farinas, etc. derived from ground wheat. Typically, hard wheat (*Triticum aestivum*) is used for bread and pasta, soft wheat (*T. aestivum*) is used for cookies, cakes and pastries (Morris & Rose, Cereal Grain Quality, Chapman & Hall, New York, N.Y., pp. 3-54 (1996)) and very hard durum wheat (*T. turgidum* ssp. *durum*) is used e.g., in pasta, bread, couscous and bulgur.

Soft wheat produces a finer granulation upon milling or grinding, hard wheat a coarser granulation, and durum wheat a very coarse granulation referred to in the art as semolina. As is well known in the art, though granulation is controlled somewhat by milling, it is highly limited by the inherent hardness characteristics of the wheat variety.

Although it is difficult to obtain a finely granulated durum wheat flour without incurring excessive starch damage and expending considerable energy, finer granulations of durum wheat flour are increasingly preferred by modern pasta manufacturers. Thus, what is needed in the art, now more than ever, is a durum wheat having grain with soft-kernel texture.

Soft textured durum wheats are known. However, the available soft textured durum wheats are either transgenic (see e.g., U.S. Pat. No. 6,596,930) or are low producing and/or genetically unstable (see e.g., Liu, C. Y. (1995) *Journal of Cereal Science* 21:209-213). Market acceptance of transgenic plants, the produce from transgenic plants, and the products made from transgenic plants is typically low. Genetically unstable wheat plants that are low yeilding and which cannot be used for the development of new wheat varieties are of limited use. Thus, the need remains for a non-transgenic durum wheat having grain with soft-kernel texture which has functional Ph1 and diploid like behavior in meiosis and which therefore can be used as a parent in a genetic cross e.g., as a foundation parent in the development of new non-transgenic tetraploid wheat plants soft textured endosperm.

Fortunately, the present inventors herein provide such a non-transgenic tetraploid wheat plant having grain with soft-kernel texture. The non-transgenic tertraploid wheat plants have functional Ph1 and diploid like behavior in meiosis and are therefore suitable to serve as a parent in a genetic cross. Thus, the non-transgenic tetraploid wheat plant having grain with soft-kernel texture and having functional Ph1 and diploid like behavior in meiosis is suitable as foundation stock for the development of new wheat varieties having grain with soft kernel texture. In some exemplary embodiments, the non-transgenic tetraploid wheat plants having functional Ph1 and diploid like behavior in meiosis have less than a whole alien chromosome substitution. In other exemplary embodiments, the non-transgenic tetraploid wheat plants having functional Ph1 and diploid like behavior in meiosis have less than a whole-arm alien chromosome translocation In an exemplary embodiment, grain from the non-transgenic tetraploid wheat plant having grain with soft-kernel texture is milled to produce high yields of durum flour with low levels of damaged starch. In another exemplary embodiment, grain from the non-transgenic tetraploid wheat plant having grain with soft-kernel texture is milled to produce durum semolina with low work expenditure compared to semolina prepared from normal very hard durum wheat.

II. Genetic Crosses to Produce a Non-Transgenic Soft Durum Wheat Plant.

A. General Methods

Methods disclosed herein utilize routine techniques in the field of wheat genetics, cytogenetics, and milling. Basic terminology in the field of genetics and cytogenetics can be found e.g., In: Robert C. King, William D. Stansfield, *A Dictionary of Genetics*, sixth edition 2002, Oxford University Press; basic texts in wheat genetics include, e.g., Alain P. Bonjean and William J. Angus, *The World Wheat Book A History of Wheat Breeding*, 2001, Lavoisier Publishing, Paris; K. S. Quisenberry and L. P. Reitz, *Wheat and Wheat Improvement*, 1967, American Society of Agronomy, Inc., Madison, Wis.

Techniques and methods for the cytological manipulation and analysis of wheat are well known to of skill in the art see e.g., Sybenga J. (1992) Cytogenetics in Plant Breeding, Monographs on Theoretical and Applied Genetics, vol. 17, Springer-Verlag, Berlin; Sharma A. K., Sharma A. (1980) Chromosome Techniques. Theory and Practice, $3^{rd}$ edn., Butterworths, London; Morris R., Sears E. R. (1967) The Cytogenetics of Wheat and Its Relatives, pp. 19-87, in Wheat and Wheat Improvement, editors Quisenberry K. S., Reitz L. P., American Society of Agronomy, Madison, Wis.; Gill B. S. (1987) Section 5E: Chromosome Banding Methods, Standard Chromosome Band Nomenclature, and Applications in Cytogenetic Analysis, pp. 243-254, in Wheat and Wheat Improvement, $2^{nd}$ edn., editor Heyne E. G., American Society of Agronomy, Madison, Wis.; Joppa L. R. (1987) Section 5F: Aneuploid Analysis in Tetraploid Wheat, pp. 255-287, in Wheat and Wheat Improvement, $2^{nd}$ edn., editor Heyne E. G., American Society of Agronomy, Madison, Wis.; Knott D. R. (1987) Section 7E: Transferring Alien Genes to Wheat, pp. 462-471, in Wheat and Wheat Improvement, $2^{nd}$ edn., editor Heyne E. G., American Society of Agronomy, Madison, Wis.

Basic terminology and technology in the field of milling can be found e.g., In: Posner E. S., Hibbs, A. N. (1997)*Wheat Flour Milling* American Association of Cereal Chemists, St. Paul, Minn.

B. Genetics of Wheat Having Soft Textured Endosperm

In *T. aestivum* wheat (bread wheat), differences in grain texture result from the expression of one major gene locus, designated *Hardness (Ha)* (see e.g., Symes K. J. (1965) *Aust J Agric Res.* 16:113-123; and Baker R. J. (1977) *Crop Sci.* 17:960-962). The hardness locus, which is located on the short arm of chromosome 5D (i.e., 5DS) (see e.g., Mattern, P. J. et al. *Proceedings of the $4^{th}$ International Wheat Genetics Symposium*. Columbia, Mo.: Univ. Missouri; 1973. pp. 703-707; and Law, C. N. et al. *Seed Protein Improvement by Nuclear Techniques*. Vienna, Austria: International Atomic Energy Agency; 1978. pp. 483-502), has two alleles: Ha (soft) and ha (hard). It is generally well accepted that two genes present at this locus, puroindoline a and puroindoline b, are the causative agents for grain softness. Mutations in either puroindoline gene result in a partial loss of kernel softness (Morris 2002, Morris and Bhave 2008), and result in what is known as 'hard' *T. aestivum* wheat.

To have a single gene locus controlling a trait is unusual in polyploid wheat. Indeed, hexaploid wheat (*T. aestivum*) is an allohexaploid (2n=6x=42 chromosomes; genomes AABBDD). Thus, typically, most genes are present in triplicated homoeologous sets, one from each genome. However, in the case of Hardness, the loci on the 5A and 5B chromosomes that were present in the diploid progenitors were lost during the formation of tetraploid wheat and thus are not expressed in *T. turgidum*. Although softness was restored to hexaploid wheat upon its allohexaploidation with the diploid *Aegilops tauschii* (2n=2x=14 chromosomes; genome DD), tetraploid wheats (e.g., durum wheats, *T. turgidum* L. ssp. *durum*) (2n=4x=28 chromosomes; genomes AABB), lack the D genome and are therefore generally much harder textured than soft hexaploid wheat, and generally harder than hard hexaploid wheat.

Control of chromosome pairing in wheat during meiosis is under complex genetic control. One gene locus, Pairing homoeologous (Ph1), which resides on the long arm of chromosome 5B in *T. aestivum* and *T. turgidum*, exerts major control by preventing the pairing of homoeologous chromosomes (e.g., chromosome 5A pairing with 5B or 5D, etc.). Two induced mutations in this gene are well known in the art (ph1b in the hexaploid wheat variety Chinese Spring, and ph1c in the tetraploid wheat variety Cappelli), the presence of either mutation relieves the restriction against homoeologous pairing such that homoeologous chromosomes can pair at some variable frequency and efficiency, resulting in crossing-over and exchange of genetic material (see e.g., Sears, E. R. (1977)*Canadian Journal of Genetics and Cytology* 19:585-593; Giorgi B. (1978) *Mut. Breed. Newsletter* 11:4-5; Jauhur P. P., Doğramaci, M., Peterson T. S. (2004) *Genome* 47:1173-1181; Gennaro A., Forte P., Carozza R. et al. (2007) *Israel Journal of Plant Sciences* 55:267-276; Qi L., Friebe B., Zhang P., Gill B. S. (2007) *Chromosome Research* 15:3-19; Luo M.-C., Yang Z.-L., Kota R. S., Dvořák J. (2000) *Genetics* 154:1301-1308; Jauhar P. P., Riera-Lizarazu O., Dewey W. G. et al. (1991)*Theoretical and Applied Genetics* 82:441-449).). This phenomenon is well known in the art as "homoeologous translocation".

Presence of ph1b affects plant morphology, decreases fertility and reduces male transmission; homozygotes frequently exhibit monosomes and trisomes, and telocentric chromosomes sometimes occur because of the irregularities associated with homoeologous pairing. Reciprocal translocations also occur but are difficult to identify due to formation of multivalents. ph1b varieties are more conveniently maintained as F1 heterozygotes, as a single functional copy of a functional Ph1 gene is sufficient to prevent homoeologous pairing.

Additional gene loci that suppress homoeologous pairing are known in the art, as are mutations that relieve that control and thereby facilitate pairing and exchange between homoeologous chromosomes (see e.g., Sears E. R. (1976) *Annual Review of Genetics* 10:31-51). Although these various genes do not act in precisely the same fashion (see e.g., Martinez M., Cuñado N., Carcelén N., Romero C. (2001)

*Theoretical and Applied Genetics* 103:398-405), any method known in the art that facilitates pairing of homoeologous chromosomes and homoeologous translocation of genetic material, specifically the transference of the Hardness locus from the short arm of chromosome 5D to either 5A or 5B or elsewhere in the genome of tetraploid wheat where the gene locus will be stably expressed, is suitable for use in the construction of non-transgenic tetraploid wheat plants having grain with soft kernel texture as disclosed herein.

As is known in the art, homoeologous translocations are highly unpredictable, variable, and are dependent on many factors such as e.g., the particular chromosome involved, the varieties being used, the locus being transferred, the location of that locus, other undesirable genes present on the translocated section of chromosome, differential gamete transmission rates, etc., and that *T. turgidum* is less tolerant of genome alterations than is *T. aestivum* (see e.g., Ceoloni C., Forte P., Gennaro A. et al. (2005) *Cytogenetic and Genomic Research* 109:328-334; Luo M.-C., Yang Z.-L., Kota R. S., Dvořák J. (2000) *Genetics* 154:1301-1308; Jauhur P. P., Dogramaci M. (2008) *Euphytica* 159:353-358; Juahur P. P., Almouslem A. B., Peterson T. S., Joppa L. R. (1999) *The Journal of Heredity* 90:437-445). As will be discussed in greater detail hereinbelow, the occurrence of both Ph1 and Hardness on the same homoeologous chromosome group (group 5 chromosomes) presents an additional complicating factor in the possible cytogenetic manipulation of these traits.

The methods disclosed herein for the construction of a non-transgenic tetraploid wheat plants having grain with soft textured endosperm utilize the variable presence or absence of chromosome 5B, the normal location of the Ph1 gene locus. Ordinarily, a 5D(5B) disomic substitution line which lacks chromosome 5B would lack the Ph1 gene which suppresses homoeologous pairing. Indeed, in the absence of chromosome 5B there is some pairing with non-homologous chromosomes. Therefore, methods disclosed herein employ a substitution line comprising a pair of 5D chromosomes and a monosome of 5B in order to prevent unwanted non-homologous pairing from occurring. The monosome is almost never passed through the male parent, thus the substitution line with the monosome 5B cannot participate in homoeologous pairing.

Although there have been some reports that allege successful construction of non-transgenic tetraploid wheat plants having grain with soft kernel texture, in each case it is apparent that the alleged non-transgenic tetraploid wheat plants having grain with soft kernel texture do not behave as diploids in meiosis, e.g., they do not show stable Mendelian segregation. (see e.g., Gazza L., Niglio A., Mei E. et al. ((2002) *Proceedings of second international workshop Durum Wheat and Pasta Quality: Recent Achievements and New Trends*, Rome, 19-20 Nov. 2002, p. 285-288; Gazza L., Zanell L., and Pogna N. E. ((2008) 11*th International Wheat Genetics Symposium* 2008, *Proceedings of the 11th International Wheat Genetics Symposium*, 24-29 Aug. 2008, Brisbane, Queensland, Australia, vol. 2, p. 339-341; Simeone M. C., Lafiandra D., Morris C. F. ((2003) *Tenth International Wheat Genetics Symposium*, 1-6 Sep. 2003, Paestum, Italy, vol. 3, p. 1391-1393).

Thus, prior to the instant disclosure, non-transgenic tetraploid wheat plants having grain with soft kernel texture wherein the non-transgenic tetraploid wheat plants having grain with soft kernel texture have a functional Ph1 and diploid-like behavior in meiosis were not known, nor had a method for the construction of said wheat plants been heretofore appreciated or disclosed.

C. "Herding Cats"—the Use of Ph1 Mutants Results in Loss of Ordered Chromosome Pairing in Meiosis and Instability of the Wheat Genome As is well known in the art, grass genomes are variably related based on their evolutionary relationships. In particular, the genomes of hexaploid and tetraploid wheat are related to the degree that their chromosomes are termed "homoeologues". Homoeologues have, variably, the ability to compensate for each other. Thus, through cytogenetic manipulations, it is possible to construct disomic substitution lines in tetraploid wheat using hexaploid wheat chromosomes.

Unfortunately, durum wheat exhibits a much lower tolerance toward genome alterations as compared to common wheat. Indeed, sizable alien transfers, even when well tolerated by the hexaploid common wheat genome, are not well tolerated by the tetraploid durum wheat genome (see e.g., Ceoloni, C. et al. (2005)*Cytogenetics and Plant Breeding* 109:328-334). For example, although tetraploid wheat plants having soft textured endosperm can be obtained by substituting the 5D chromosomes from hexaploid wheat for 5A or 5B in tetraploid wheat such disomic substitution lines are typically lower in grain yield and vigour and may be sterile (see e.g., Liu et al. (1995) *Journal of Cereal Science* 21:209-213).

Thus, whole chromosome substitutions or even Robertsonian whole arm translocations are not typically desirable as parents in breeding stable tetraploid wheat cultivars because, 1) the alien chromosome or arm will not pair during future breeding efforts e.g., an introduced 5D will have nothing to pair with nor will the 5A or 5B of the other parent depending on the substitution, and 2) linkage drag—the association of undesirable genes on the same chromosome or arm as the gene/trait of interest (see e.g., Qi, L. et al. (2007) *Chromosome Research* 15:3-19).

Linkage drag is thought to result from restrictions upon pairing between homoeologous chromosomes. Thus, the transfer of a target gene from a wild relative (often referred to as alien) to a crop plant is difficult, because transfer of the desired target gene is accompanied by the transfer of other untargeted wild traits that are due to genes also present in the transferred chromosome segment.

As is well known in the art, the problem of linkage drag and non-acceptance of alien chromosome is typically overcome by removing the controlled pairing of homoeologues exerted by the Ph1 gene locus. The Ph1 can be removed by removing the entire 5B chromosome, removing the long arm of 5B, or deleting some smaller portion of 5BL via irradiation. Two exemplary radiation-induced mutants are the hexaploid wheat ph1b and the tetraploid wheat ph1c. In wheat plants lacking Ph1 control, homoeologues may pair, form chiasmata and exchange genetic material.

Movement of traits from one genome to another by removing Ph1 control is referred to as "homoeologous translocation." Typically, at some point after homoeologous translocation is effected, Ph1-mediated control must be restored by replacing the mutation with the functional gene locus so as to stablize the newly created line.

Indeed, it is well known in the art that the use of Ph1 mutants is highly unpredictable (see e.g., Qi, L. et al. (2007) supra; Sears, E. R. (1977) *Canadian Journal of Genetics and Cytology* 19:585-593). The lack of Ph1 control permits homoeologous pairing and recombination, which can vary between different chromosomes of a species, and between the short and long arms of a chromosome. Furthermore, wheat plants lacking Ph1 control experience a high frequency of recombination between non-designated homoeologues as well as non-homologous pairing. Thus, the products of meiosis and the progeny resulting therefrom are highly unpredictable (see e.g., Qi, L. et al. (2007) supra, Jauhar, P. P. and Dogramaci, M. (2008) *Euphytica* 159:353-358). Thus, Ph1 mutant parent lines are inherently unstable and progeny of Ph1 mutant parents typically suffer chaotic chromosome rearrangements. Indeed, as a result of the irregularities associated with homeologous pairing, progeny of Ph1 mutant parents are known to carry monosomes and trisomes at high frequency, as well as telocentric chromosomes and other chromosome irregularities (see e.g. Sears, E. R. (1977) supra).

Since the Ph1 locus is on the 5B chromosome, attempts at homoeologous translocations involving group 5 chromosomes are especially unpredictable. Although this general approach (homoeologous translocation) has proven successful in tetraploid wheat, a much greater and further complication results when the gene/trait of interest lies in one of the homoeologous group 5 chromosomes as does the gene conferring soft textured kernels which is located on chromosome 5D (see e.g., Joppa, L. R., and Williams, N. D. (1983) "Genetics and breeding of durum wheat in the United States." In Durum Wheat: Chemistry and Technology. Eds. G. Fabriani and C. Lintas, American Association of Cereal Chemists, Inc., St. Paul, Minn., Chapter 3, pp. 47-67; Sears, E. R. (1976) *Annual Reviews Genetics* 10:31-51; Sears, E. R. (1977) supra).

Since chromosomal rearrangements, unbalanced genomic constitutions, aneuploidies, structural and intergenomic rearrangements are commonplace in wheat plants lacking Ph1 control (see e.g., Sánchez-Moran et al. (2001) *Chromosoma* 110:371-377) and since both the Ph1 locus and the softness locus are located on the group 5 chromosomes, predicting the outcome from crosses employing a homeologous translocation of the 5D chromosome into tetraploid wheat is so to speak, tantamount to "herding cats".

D. Construction of a Non-Transgenic Tetraploid Wheat Plant Having Soft Textured Endosperm Using Classical Breeding Techniques It has now been discovered that teraploid wheat plants that produce wheat grain having a soft texture (soft textured endosperm) can be constructed using classical and cytogenetic breeding techniques. In an exemplary embodiment, a non-transgenic tetraploid wheat plant having soft textured endosperm is a durum wheat plant.

In general, the goal of wheat breeding is to develop new, unique and superior wheat varieties. In practical application of a wheat breeding program, a breeder initially selects and crosses two or more parental lines, followed by repeated selfing and selection, producing many new genetic combinations. Theoretically billions of different genetic combinations can be generated via crossing, selfing and mutations. An exemplary method for constructing a non-transgenic durum wheat plant having soft textured endosperm is disclosed hereinbelow.

ABBREVIATIONS/DEFINITIONS

LDN=Langdon
CS=Chinese Spring
CS-5D(5B)=CS carrying a disomic substitution where 5D have replaced 5B
CS(ph1b)=CS carrying the ph1b mutation
LDN-ddt-5B=LDN double ditelosomic 5B
ph1b=Pairing homoeologous-1 gene with deletion (=b allele)
Stocks:
LDN-47-1 with ph1b from CS (maintained as an $F_1$ heterozygote)
LDN-16
LDN double ditelosomic 5B
LDN-5D(5B) substitution line
Pedigrees:
LDN-5D(5B) substitution line: CS-5D(5B)/*12 LDN-16
LDN-47-1 ph1b line: CS(ph1b)/*2 LDN-16//2*LDN-47-1 [$F_2$ seed, maintained as a heterozygote]
Step 1:
Cross 'LDN-5D(5B)'×'LDN-47-1' (disomic substitution line with the ph1b mutant line).
Results:
$F_1$ plant(s) that is(are) monosomic for both 5D and 5B; some of the progeny will also have ph1b.
Step 2:
Grow F1 plants, select plants with 2n=28 chromosomes. Those with 13 bivalents+2 monovalents do not carry ph1b, whereas those with variable pairing do carry ph1b; self-fertilize; those plants with ph1b will have homoeologous pairing between 5D and 5B and crossing-over (creating translocation(s)).
Step 3:
Harvest $F_2$ seeds; select plants with variable pairing that carry ph1b. In some cases, at least some of the plants will have cells in which at least one of the chromosomes will fail to form ring bivalents. This may indicate that one of the chromosomes is a translocation between 5B and 5D.
Step 4:
Cross selected $F_2$ plants to a "normal durum" (for example, crossing to Langdon represents $BC_1$).
Step 5:
Select $BC_1F_1$ plants with 13 pairs of chromosomes at metaphase I of meiosis and variable pairing; self fertilize.
Step 6:
Grow $BC_1F_2$ plants.
Step 7a: 'Test' Cross (verify translocation vs. a 5D disomic substitution)
Cross $BC_1F_2$ plants with LDN-ddt-5B.
Step 7b:
Grow progeny. At least three types of progeny are expected. If the parent had a pair of 5D chromosomes (a substitution, not a translocation), then the 5B telosomic chromosomes will fail to pair. If the parent had a pair of 5B chromosomes, then both telosomic chromosomes will pair. If the parent had a translocation, then only one of the telosomic chromosomes will pair (the 5BL).
Step 7c:
Select plants with 13 bivalents=1 telomeric bivalent+1 telomeric monovalent (plants with translocation). Discard plants with 13 bivalents+trivalent with one whole chromosome and two telosomic chromosomes, one for each arm all paired together, in short hand notation, t1t''', i.e., a 5D disomic substiution).
Step 8:
Cross to LDN-5D(5B) substitution line and look for the parents in which only one of the chromosomes fails to form ring bivalents. Select parents based on this cytological analysis; grow and self-fertilize.

The above protocol shows exemplary steps taken to construct a non-transgenic tetraploid wheat plant having grain with soft kernal texture. As will be appreciated by a person having skill in the art, other durum wheats other than Langdon, can be used (if available). A person of skill in the art also well appreciates that ph1c or other means to relieve homoeologous pairing restrictions could be used. Disomic substitutions other than Chinese Spring are also suitable, provided the 5D carries to the Hardness locus with expressed Pina and Pinb. As will be readily appreciated by a person of skill in the art, the key is the "composition" and nature of the stocks and how they are used sequentially, not the exact variety background in which they exist.

III. Measuring Endosperm Texture

Grain texture classification is based primarily on either the resistance of kernels to crushing or the particle size distribution of ground grain or flour. Because kernel texture is important for wheat grain quality and utilization, numerous methods have been developed to measure grain texture (see e.g., Pomeranz, Y. and Williams, P. C. (1990) *Wheat hardness: Its genetic, structural, and biochemical background, measurement, and significance*. Pages 471-548 In: *Advances in Cereal Science and Technology*, Vol. X. Y. Pomeranz, ed. AACC International: St. Paul, Minn.; Glenn, G. M. et al. (1991) J. Cereal Sci. 13:179-194; Haddad et al. (1998) Cereal Chem. 75:673-676; Morris (2002) Plant Mol. Biol. 48:633-347; Morris, C. F. et al. (2007) Cereal Chem. 84:67-69; Morris, C. F. et al. (2008) Cereal Chem. 85:351-358; Pearson, T. et al. (2007) Cereal Chem. 84:567-575.

Typically, methods for measuring grain hardness measure either: (1) the size and distribution of particles after grinding or milling, or (2) directly measure the compressive strength of kernels.

Exemplary methods for measuring the size and distribution of particles after grinding or milling include, but are not limited to the particle size index (PSI) (see e.g., Williams, P. C. and Sobering, D. C. (1986) Cereal Foods World 31:359, 362-364 (Approved Method 55-30, AACC International 2000); and near infra-red (NIR) spectroscopy (see e.g., Norris, K. H. et al. (1989) Cereal Foods World 34:696-705 (Approved Method 39-70A, AACC International 2000).

Exemplary methods for directly measuring the compressive strength of kernels include, but are not limited to automated weighing and crushing of individual kernels (see e.g., Martin, C. R. et al. (1993) Trans. ASAE 36:1399-1404). Instruments capable of directly weighing and crushing Individual kernels are available and known to those of skill in the art. For example, the single kernel characterization system (SKCS) model 4100 (Perten Instruments, Springfield, Ill.) (AACC Approved Method 55-31) is effective for carrying out measurement of the compressive strength of kernels.

In an exemplary embodiment, wheat grain having soft textured endosperm is measured according to the Perten SKCS 4100 (Perten Instruments, Reno, Nev. See e.g., Instruction Manual, Single-Kernel Characterization System, Model SKCS 4100; Perten Instruments, Inc.: 6444 South Sixth Street Road, Springfield, Ill. 62707) and has a hardness index/value of between about 10 to about 45 on a scale of −20 to 120. In other exemplary embodiments, the kernel hardness associated with grain of soft wheats have SKCS hardness values in a range that is from about 0 to about 55. In other exemplary embodiments, the grain of a non-transgenic tetraploid wheat plant having soft textured endosperm have SKCS hardness values in a range that is from about 15 to about 35. In stll other exemplary embodiments, the grain of a non-transgenic tetraploid wheat plant having soft textured endosperm has a hardness value that is in a range that is between about 10 to about 45 as measured by the Perten SKCS 4100.

IV. Preparing Semolina, Flour and Pasta

In exemplary embodiments, soft textured grain produced by a non-transgenic tetraploid wheat plant as disclosed herein, is milled to prepare durum flour and/or semolina.

Wheat grain is rarely consumed whole and as such, is first converted to granular products via milling. Wheat grain milling is largely dependent on kernel texture and thus, a mill is typically designed to mill exclusively soft wheat, hard wheat or durum wheat, in some instances a mill may be a "swing" mill such that it can, at lower efficiency, mill both soft and hard wheats.

Typically durum wheat is milled to produce a product of coarse granulation called semolina (see e.g., CFR §137.320); the production of durum flour (see e.g., CFR §137.220) is not a primary objective but cannot be wholly prevented as some few grain particles will be of insufficiently small size to be construed as flour. Pasta manufacturers prefer finer granulations and durum flour receives little if any monetary discount in the trade. The primary obstacle to producing a greater proportion of durum flour relative to semolina resides in the greater work involved in obtaining the finer granulation and the inherent greater level of damaged starch as work input increases (see e.g., Posner, E. S., and Hibbs, A. N. (1997) *Wheat Flour Milling*. St. Paul, Minn.: American Association of Cereal Chemists, Inc.).

Methods for preparing semolina are known in the art (see e.g., U.S. Pat. No. 5,141,764; U.S. Pat. No. 7,506,829; Approved Method 26-42, AACC International 2000).

In an exemplary embodiment, durum wheat is milled to produce coarse, granular particles of semolina. Typically, in the production of durum semolina, it is desirable to minimize the production of durum flour. Therefore, the primary difference between flour and semolina milling is the method and degree of grinding of the endosperm. In general flour is finely ground, whereas semolina is coarsely ground.

In an exemplary embodiment, the semolina prepared from soft textured endosperm produced by a non-transgenic tetraploid wheat plant as disclosed herein, is used for making pasta. Pasta manufacturing is known in the art (see e.g., U.S. Pat. No. 6,326,049; U.S. Pat. No. 3,520,702; U.S. Pat. No. 6,322,840; U.S. Pat. No. 6,203,840).

As is known in the art, pasta manufacturers typically prefer the majority of particles to fall within a narrow particle size range to insure that semolina will flow freely, and that pasta dough water uptake will be homogeneous (see e.g., Feillet, P. and Dexter, J. (1996) Quality requirements of durum wheat for semolina milling and pasta production. Pp. 95-131 In: Pasta and Noodle Technology. Kruger, J., Matsuo, R. and Dick, J., editors, American Association of Cereal Chemists. St. Paul, Minn.).

In an exemplary embodiment grain from a non-transgenic tetraploid wheat plant having grain with soft kernel texture is milled to flour wherein the resulting flour has low levels of damaged starch. In another exemplary embodiment, grain from a non-transgenic tetraploid wheat plant having grain with soft kernel texture is milled to produce durum semolina with low work expenditure.

V. Measuring Starch Damage

Some starch granules are mechanically damaged during the milling process. Damage is typically manifest as physical cracks and breaks in the starch granule. Since the level of starch damage directly affects water absorption, dough mixing properties and other qualities of the milled product e.g., semolina, flour, etc., starch damage is of technological significance. Thus, it is useful to be able to characterize starch damage in terms of both quantity and quality.

In general, the greater the compressive and shearing forces to achieved a granular milled product e.g., semolina, flour, etc, the more starch damage may be incurred. Thus, typically harder textured grain which requires the application of greater compressive and shearing forces to achieve a milled granular product, typically experiences greater starch damage during milling than a softer textured grain.

Methods for measuring starch damage are known in the art. Most methods can be grouped in general, into four classes:

extraction procedures ("Blue Value"), dye-staining procedures, NIR procedures, and enzyme digestion procedures (see e.g., Williams, P., and Fegol, K. (1969) Cereal Chemistry 46, 56-6; Chiang, B., et al. (1973) Cereal chemistry 50:44-49; Medcalf, D. and Gilles, K. (1965) Cereal Chemistry 42:546-557. A. D. Evers, and D. J. Stevens (2006) Starch 40(8):297-299; Evers, A. D. and Stevens, D. J. (1985). "Starch Damage" In: "Advances in Cereal Science and Technology" Vol. VII. (Pomeranz, Y. Ed.) American Association of Cereal Chemists Inc. St. Paul Minn., pp. 321-349; Gibson, T. S., Al Qalla, H. and McCleary, B. V. (1991) J. Cereal Sci., 15, 15-27; Gibson, T. S., Kaldor, C. J. and McCleary, B. V. (1993) Cereal Chem., 70:47-51; American Association of Cereal Chemists (AACC) Approved Method 76-31).

Any method known in the art for measuring starch damage is suitable for use in the methods disclosed herein. A person having skill in the art and access to the instant specification will appreciate and choose the method best suited to their circumstances for the purpose of determining starch damage.

In one exemplary embodiment, starch damage is determined using AACC Method 76-31 Damaged Starch: Spectrophotometric Method (see e.g., Approved Methods of the American Association of Cereal Chemists (AACC), 10th Edition, 2003) and starch damage is expressed as a percentage of flour weight. AACC Method 76-31 is sometimes referred to as the Megazyme method.

In another exemplary embodiment, starch damage is determined using AACC Method 76-30A Damaged Starch.

VI. Deposit Information

A deposit of the non-transgenic tetraploid durum wheat strain having soft textured endosperm, Soft Svevo Durum Wheat WAS 080240001, disclosed hereinbelow and recited in the appended claims has been made with the American Type Culture Collection (ATCC), Patent Depository, 10801 University Blvd., Manassas, Va. 20110, U.S.A. The date of deposit was May 27, 2009. All restrictions upon the deposit have been removed, and the deposit is intended to meet all of the requirements of 37 C.F.R. 1.801-1.809. The ATCC accession number is PTA-10087. The material description is: Durum Wheat from Italy, Soft Svevo durum wheat WAS 080240001. The deposit will be maintained in the depository for a period of 30 years, or 5 years after the last request, or for the effective life of the patent, whichever is longer, and will be replaced as necessary during that period.

The following examples are offered to illustrate, but not to limit the invention.

EXAMPLES

Example 1

The following example illustrates construction and testing of a non-transgenic tetraploid wheat plant having soft textured endosperm using classical genetic techniques. In particular the following Example illustrates construction of the line known as: Soft Svevo Durum Wheat, WAS 080240001, which was deposited with the American type Culture Collection on May 27, 2009 and which has been assigned ATCC accession number is PTA-10087.

Fourteen (14) putative non-transgenic soft textured durum wheat grain varieties, bearing a putative homoeologous translocation were produced. Six of these being identified as '674', '675', '678', '679', '685', and '688', were used as disclosed hereinbelow. Each of the six above referenced putative non-transgenic soft textured durum wheat grain varieties was crossed to the durum wheat cultivars Svevo and Creso, and the progeny of each was evaluated for soft kernel texture using the Perten SKCS 4100. Results are provided in FIGS. 2-13 and hereinbelow.

ABBREVIATIONS/DEFINITIONS

LDN=Langdon
CS=Chinese Spring
CS-5D(5B)=CS carrying a disomic substitution where 5D have replaced 5B (same as CS Nullisomic 5B/Tetrasomic 5D)
CS(ph1b)=CS carrying the ph1b mutation (the ph1b mutation allows homeologous pairing)
LDN-dbl ditelo-5B=LDN double ditelosomic 5B
LDN-47-1=LDN with ph1b from CS (maintained as an $F_1$ heterozygote due to the presense of ph1b mutation)
ph1b=Pairing homoeologous-1 gene with deletion (=b allele)
Stocks:
LDN-47-1
LDN-16
LDN dbl ditelo-5B
LDN-5D(5B) disomic substitution line. The LDN-5D(5B) line is preferably maintained with a 5B monosome and is used as male in crosses. Normally, a 2n=28 disomic addition line Langdon (LDN)-5D(5B) would have no 5B chromosome, and therefore no functional Ph1, thus its genome is "unstable" each time the genome experiences meiosis. This phenomenon is discussed e.g., in Section II C. hereinabove "Herding Cats". Therefore it is preferably maintained with a 5B monosome (2n=29). Use of the Langdon (LDN)-5D(5B) strain with a 5B monosome as a male in crosses ensures that the monosome is not transmitted to the progeny since the monosome is not transmitted in the pollen. Thus, maintenance of LDN-5D(5B) with a 5B monosome and its use as the male in crosses ensures success in creating the non-transgenic tetraploid wheat plants having grain with soft textured endosperm as disclosed herein.

Pedigrees:
LDN-5D(5B) disomic substitution line: CS-5D(5B)/*12 LDN-16
LDN-47-1 ph1b line: CS(ph1b)/*2 LDN-16//2*LDN-47-1 [$F_2$ seed, maintained as a heterozygote, which will facilitates construction of the non-transgenic tetraploid wheat plants having grain with soft textured endosperm as disclosed herein.]

An exemplary series of crosses used to produce non-transgenic tetraploid wheat plants having soft textured endosperm is disclosed hereinbelow:

Step 1:
'LDN-5D(5B)'×'LDN-47-1' were crossed (i.e., disomic substitution line crossed with the ph1b mutant line).
The resulting $F_1$ plants were monosomic for both 5D and 5B; some of the progeny also carried ph1b.

Step 2:
The F1 plants produced in Step 1, were grown and plants with 2n=28 chromosomes were selected by methods known in the art. Common techniques include, but are not limited to e.g., preparing root tip squashes with staining and visualization of chromosomes (see e.g. R. J. Singh, (2003) Plant Cytogenetics, $2^{nd}$ Edition, CRS Press, Boca Raton). Plants with 13 bivalents+2 monovalents do not carry ph1b, whereas those with variable pairing do carry ph1b. Plants were self-fertilized. Those plants with ph1b experience homoeologous pairing between 5D and 5B and crossing-over (creating translocation(s)).

Step 3:

F$_2$ seeds were harvested and plants with variable pairing which therefore carry ph1b were selected. In some cases, at least some of the plants had cells in which at least one of the chromosomes will fail to form ring bivalents (see e.g., N. S. Cohn, 1969, Elements of Cytology, $2^{nd}$ Edition, Harcourt, Brace & World, Inc., New York; R. J. Singh (2003) supra) suggesting that one of the chromosomes was a translocation between 5B and 5D.

Step 4:

The selected F$_2$ plants carrying ph1b, were crossed to a Langdon durum (represents BC$_1$).

Step 5:

BC$_1$F$_1$ plants with 13 pairs of chromosomes at metaphase I of meiosis and variable pairing were selected using methods known in the art (see e.g., R. J. Singh (2003) supra; K. S. Quisenberry and L. P. Reitz (1967) supra) and the selected plants were self fertilized.

Step 6:

F2 plants from the self fertilization in step 5 i.e., BC$_1$F$_2$ plants, were grown to maturity.

Step 7a:

"Test Crosses" were conducted to determine if the selected BC$_1$F$_2$ plant carried a translocation vs. a 5D disomic substitution.

Thus, BC$_1$F$_2$ plants were crossed with LDN dbl ditelo-5B.

As is appreciated by a person of skill in the art, If the entire 5D is there (disomic substitution, then both the long arm and short arm ditelos will fail to pair with it, in the 'squash' under the microscope one sees the two arms and the 5D monosome—none paired. If it was a 5B disomic substitution (whole 5B present), then both the 5BS and 5BL ditelos can pair with the 5B whole. 5BS/5DS translocations (with Hardness), then 5BL will pair with the translocated chromosome (the long arm of 5B should still be intact), BUT the presence of the 5DS bit will prevent the 5BL ditelo from pairing.

Step 7b:

Progeny from the test cross in 7a were grown to maturity. At least three types of progeny are expected. As is appreciated by a person of skill in the art, If the entire 5D is there (disomic substitution, then both the long arm and short arm ditelos will fail to pair with it, in the 'squash' under the microscope one sees the two arms and the 5D monosome—none paired. If it was a 5B disomic substitution (whole 5B present), then both the 5BS and 5BL ditelos can pair with the 5B whole. 5BS/5DS translocations (with Hardness), then 5BL will pair with the translocated chromosome (the long arm of 5B should still be intact), BUT the presence of the 5DS bit will prevent the 5BL ditelo from pairing. In general, for reasons discussed in detail herein above, see Section II. C. "Herding cats", progeny having a whole pair of 5D chromosomes or a whole-arm of 5D chromosomes are considered unsuitable for breeding.

Step 7c:

Plants with 13 bivalents=1 telomeric bivalent+1 telomeric monovalent (i.e., the plants with a translocation) were selected. Plants with 13 bivalents+trivalent with one whole chromosome and two telosomic chromosomes, one for each arm all paired together, in short hand notation, t1t''', i.e., a 5D disomic substiution were discarded.

Step 8:

The plants selected in step 7c, were crossed to LDN-5D (5B) disomic substitution line and were examined to determine the parents in which only one of the chromosomes failed to form ring bivalents using cytological methods known in the art (see e.g., R. J. Singh (2003) supra). The parents in which only one of the chromosomes failed to form ring bivalents were selected on the cytological analysis. Selected plants were grown to maturity and were self-fertilized. F3:4 seeds were harvested.

Step 9:

We obtained a total of 438 F$_{3:4}$ seeds from 14 F$_3$ experimental lines. Approximately half of the seeds of each line (total=170 seeds) were used to grow plants in the greenhouse. Approximately half the plants were sterile and a significant proportion died of low vigor. Some plants, on the other hand, were highly vigorous. Vigor was independent from the F$_3$ line origin. These plants were used as pollinators in crossing to the Italian durum cultivars Svevo and Creso. Successful hybridizations produced 308 F$_1$ kernels (132 from Creso, 176 from Svevo).

The F3:4 progeny were grown to maturity, self fertilized, and the F3:5 seed was harvested. This process produced 14 putative Langdon durum homoeologous translocation lines, six of which are referred to herein as '674', '675', '678', '679', '685', and '688' were used in crosses to Creso and Svevo.

Step 10:

The same F3:4 progeny were grown and were "Test Crossed" to Svevo and Creso durum cultivars. F1 seed was harvested and F1 plants were grown to maturity and self fertilized. F2 seed was harvested on a per plant basis; and kernel texture phenotype was assessed. Specifics of the "Test Crosses" are discussed below.

F3:5 non-vitreous appearing kernels of Langdon durum homoeologous translocation lines 678 and 683, ten plants each, were increased in a greenhouse to produce F6 seed. Seed from the ten plants of each of the two lines was bulked and evaluated for SKCS kernel texture. The result was Hardness Indexes of 34.4±30.5 for 678 and 41.0±32.8 for 683, indicating that both were likely heterogeneous for soft and hard kernels, based on the moderately low means and markedly high standard deviations.

Figure 2:
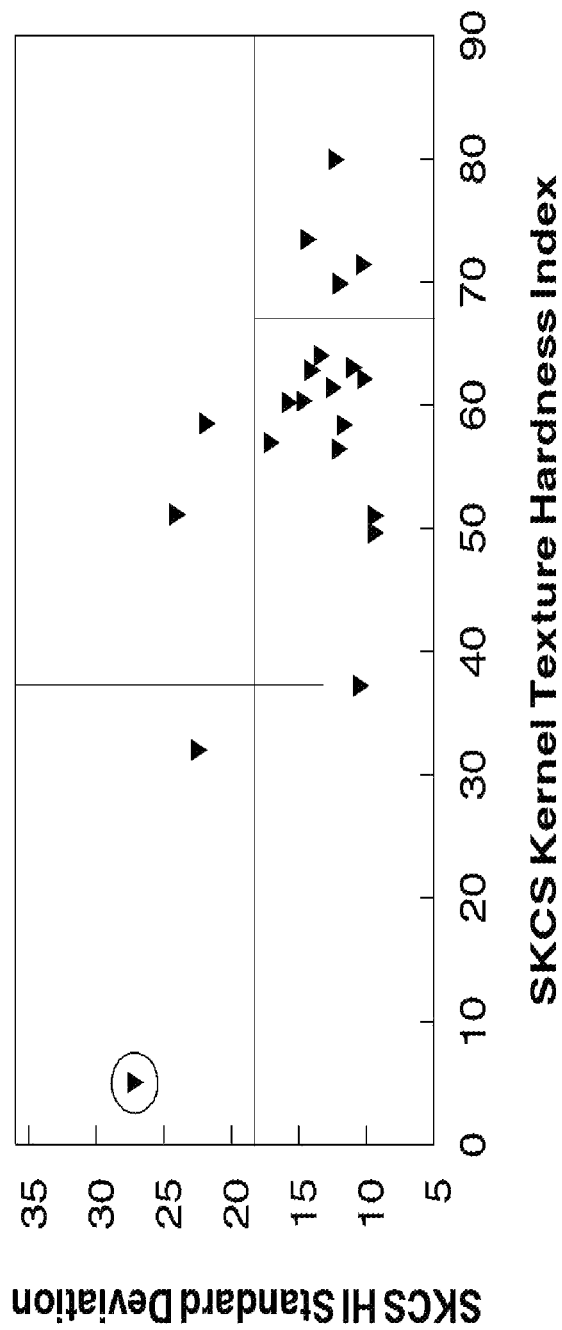
FIG. 2. Plot of SKCS kernel texture Hardness Index (HI) versus SKCS HI standard deviation of F2 kernels harvested from individual F1 plants derived by crossing the Italian durum wheat cultivar Svevo (filled triangles) with non-transgenic Langdon durum homoeologous translocation line '674' F3:4 plants as male. Lines indicate suggested delineations in kernel texture phenotypic classes. The circled symbol identifies soft durum progeny translocation line'152' which was selected and used to develop 'Soft Svevo Durum Wheat WAS 080240001' which was deposited with the American Type Culture Collection under Accession number PTA-10087.
Figure 3:
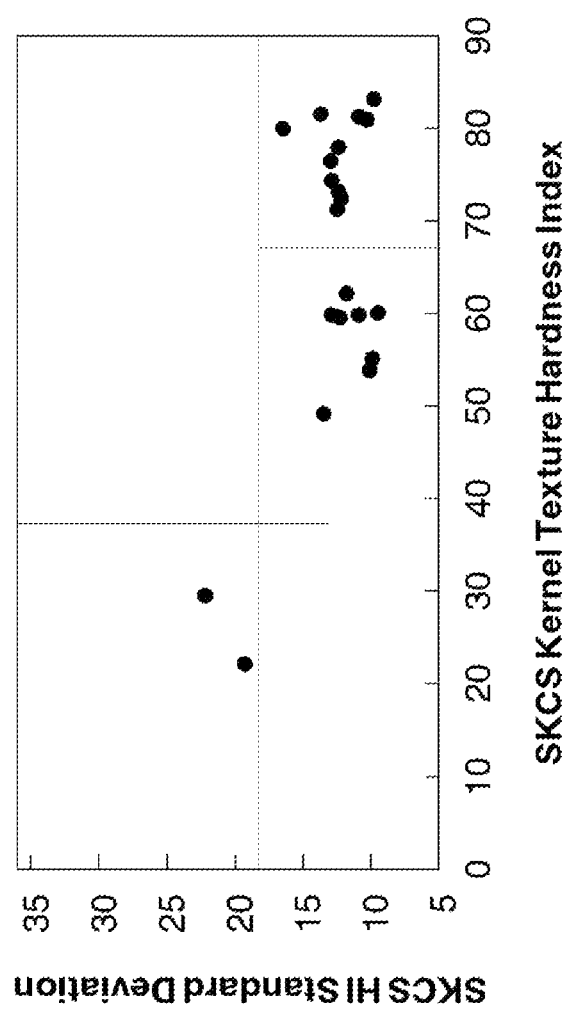
FIG. 3. Plot of SKCS kernel texture Hardness Index (HI) versus SKCS HI standard deviation of F2 kernels harvested from individual F1 plants derived by crossing the Italian durum wheat cultivar Creso (filled circles) with non-transgenic Langdon durum homoeologous translocation line '674' F3:4 plants as male. Lines indicate suggested delineations in kernel texture phenotypic classes.
Figure 4:
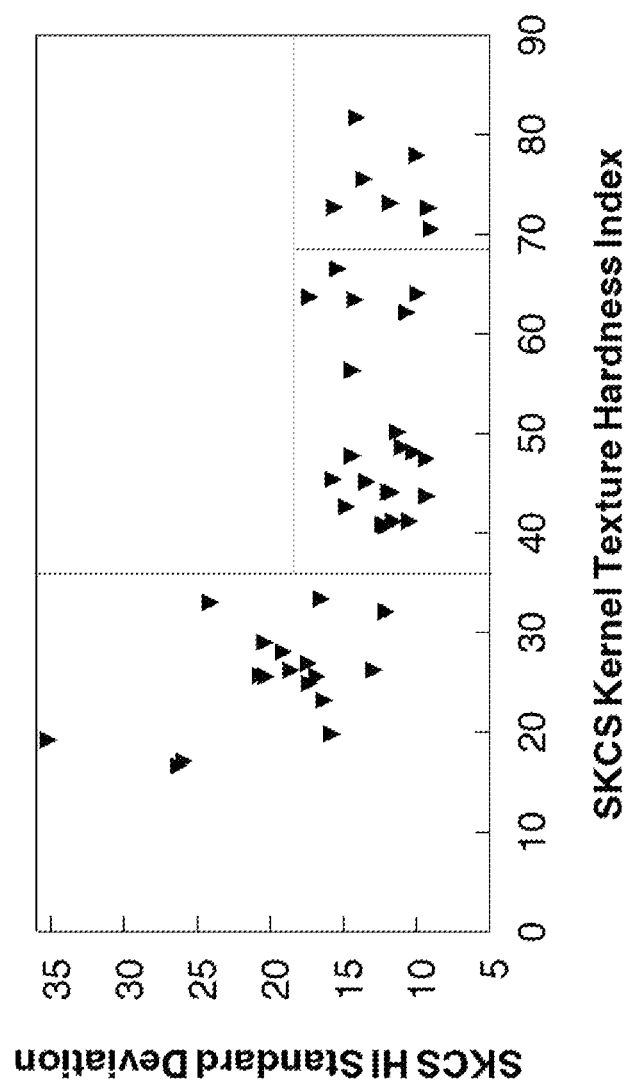
FIG. 4. Plot of SKCS kernel texture Hardness Index (HI) versus SKCS HI standard deviation of F2 kernels harvested from individual F1 plants derived by crossing the Italian durum wheat cultivar Svevo (filled triangles) with non-transgenic Langdon durum homoeologous translocation line '675' F3:4 plants as male. Lines indicate suggested delineations in kernel texture phenotypic classes.
Figure 5:
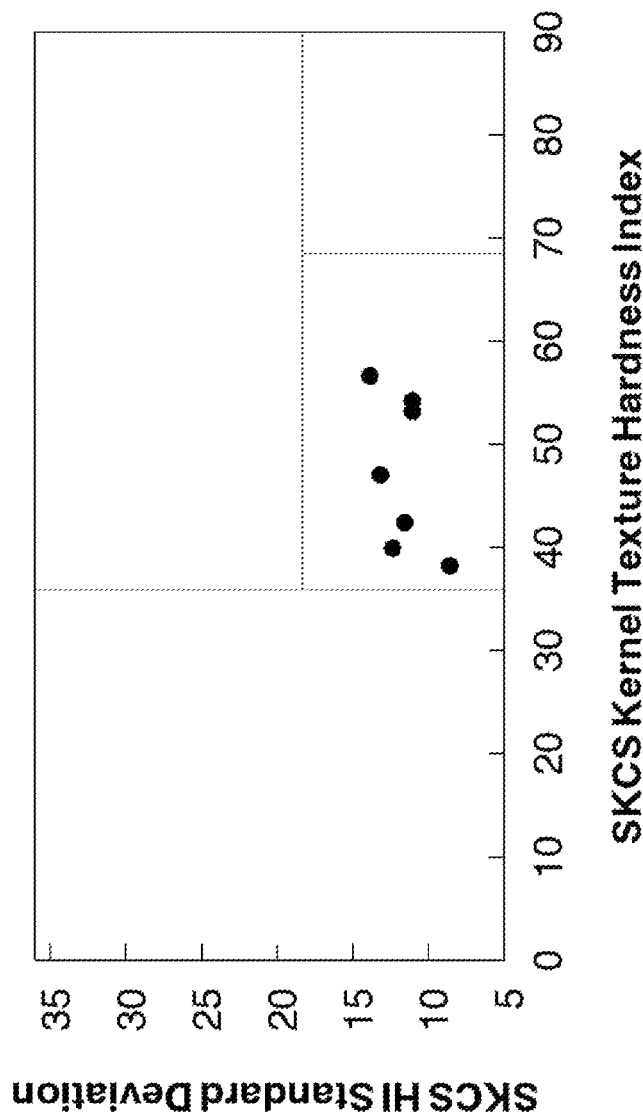
FIG. 5. Plot of SKCS kernel texture Hardness Index (HI) versus SKCS HI standard deviation of F2 kernels harvested from individual F1 plants derived by crossing the Italian durum wheat cultivar Creso (filled circles) with non-transgenic Langdon durum homoeologous translocation line '675' F3:4 plants as male. Lines indicate suggested delineations in kernel texture phenotypic classes.
Figure 6:
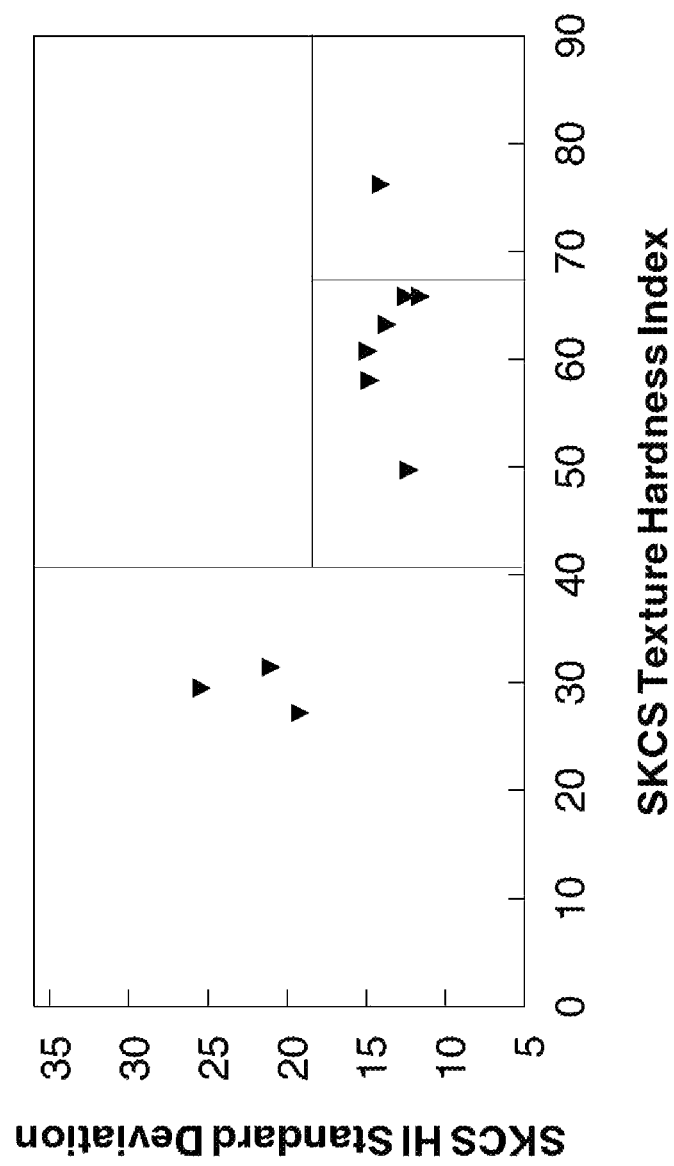
FIG. 6. Plot of SKCS kernel texture Hardness Index (HI) versus SKCS HI standard deviation of F2 kernels harvested from individual F1 plants derived by crossing the Italian durum wheat cultivar Svevo (filled triangles) with non-transgenic Langdon durum homoeologous translocation line '678' F3:4 plants as male. Lines indicate suggested delineations in kernel texture phenotypic classes.
Figure 7:
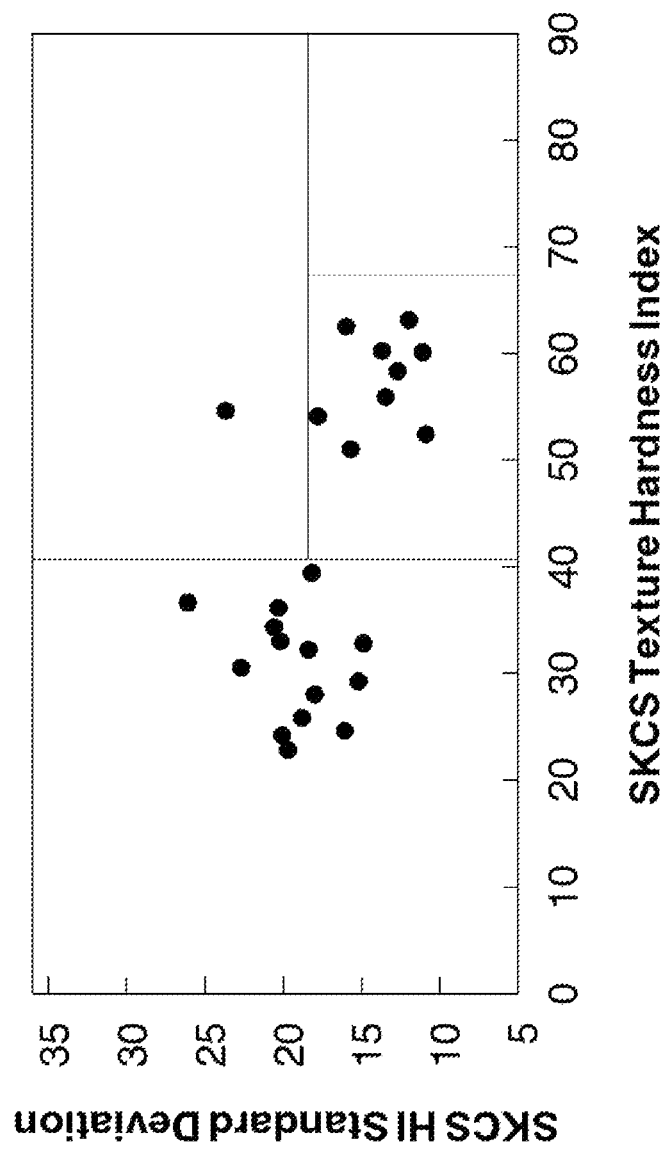
FIG. 7. Plot of SKCS kernel texture Hardness Index (HI) versus SKCS HI standard deviation of F2 kernels harvested from individual F1 plants derived by crossing the Italian durum wheat cultivar Creso (filled circles) with non-transgenic Langdon durum homoeologous translocation line '678' F3:4 plants as male. Lines indicate suggested delineations in kernel texture phenotypic classes.
Figure 8:
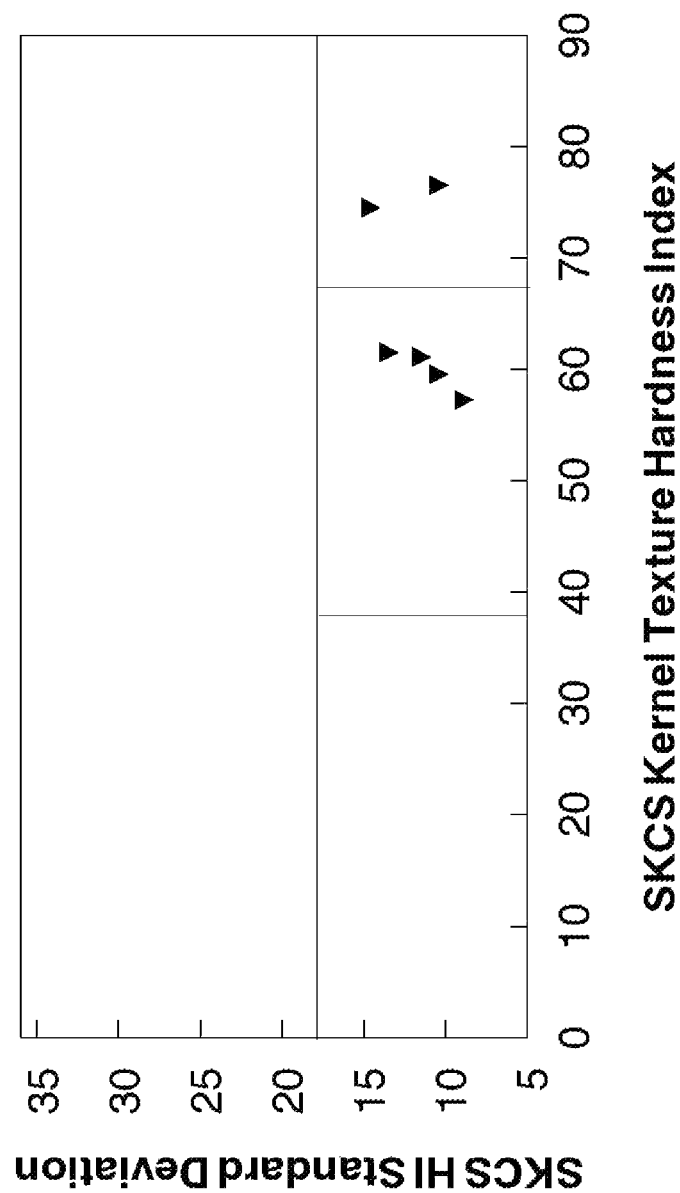
FIG. 8. Plot of SKCS kernel texture Hardness Index (HI) versus SKCS HI standard deviation of F2 kernels harvested from individual F1 plants derived by crossing the Italian durum wheat cultivar Svevo (filled triangles) with non-transgenic Langdon durum homoeologous translocation line '679' F3:4 plants as male. Lines indicate suggested delineations in kernel texture phenotypic classes.
Figure 9:
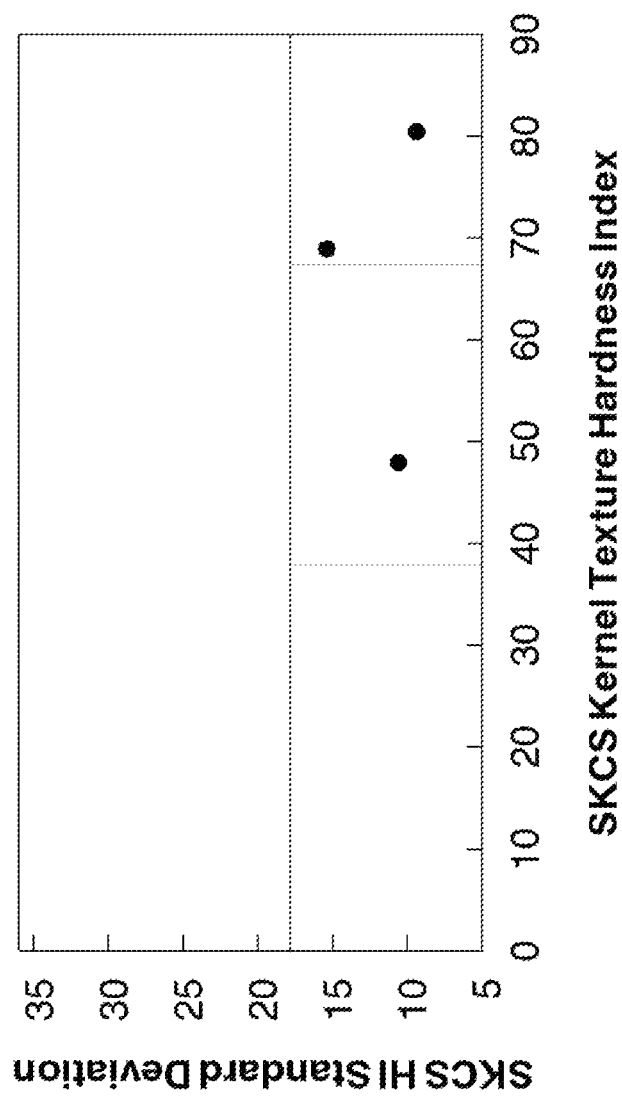
FIG. 9. Plot of SKCS kernel texture Hardness Index (HI) versus SKCS HI standard deviation of F2 kernels harvested from individual F1 plants derived by crossing the Italian durum wheat cultivar Creso (filled circles) with non-transgenic Langdon durum homoeologous translocation line '679' F3:4 plants as male. Lines indicate suggested delineations in kernel texture phenotypic classes.
Figure 10:
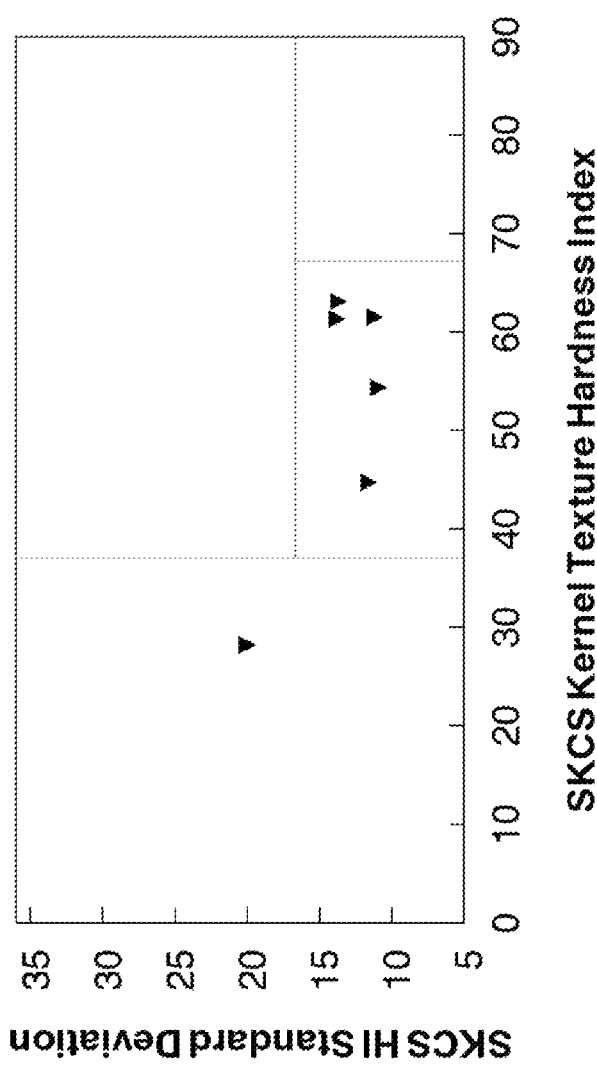
FIG. 10. Plot of SKCS kernel texture Hardness Index (HI) versus SKCS HI standard deviation of F2 kernels harvested from individual F1 plants derived by crossing the Italian durum wheat cultivar Svevo (filled triangles) with non-transgenic Langdon durum homoeologous translocation line '685' F3:4 plants as male. Lines indicate suggested delineations in kernel texture phenotypic classes.
Figure 11:
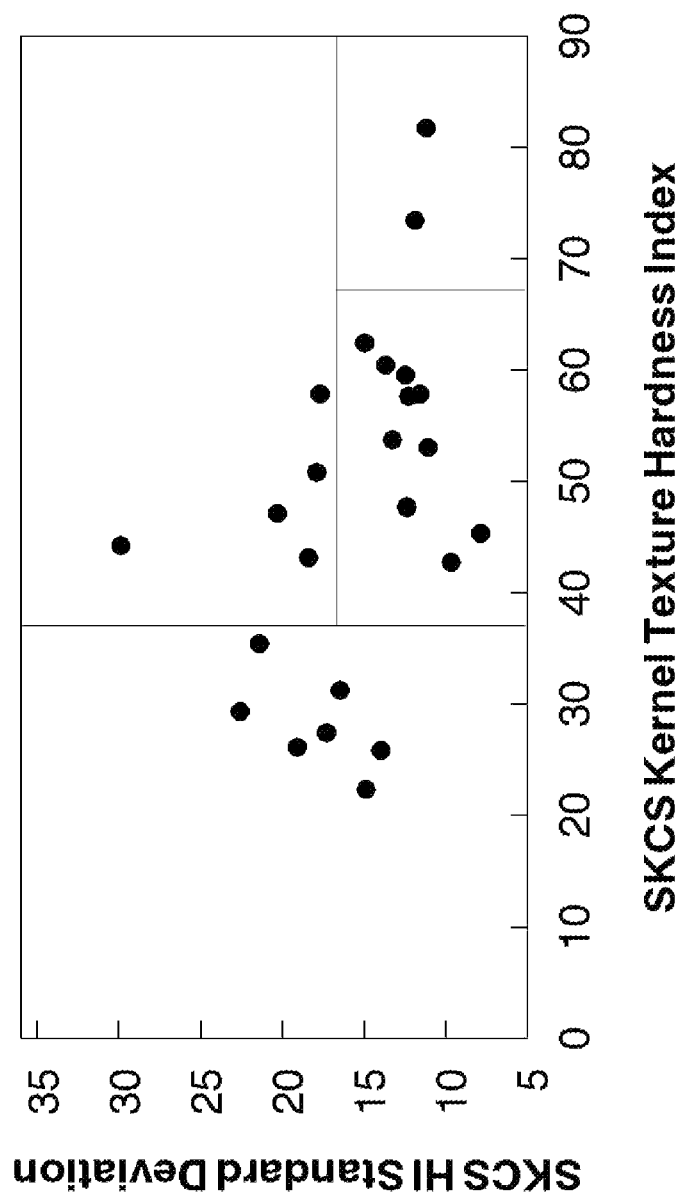
FIG. 11. Plot of SKCS kernel texture Hardness Index (HI) versus SKCS HI standard deviation of F2 kernels harvested from individual F1 plants derived by crossing the Italian durum wheat cultivar Creso (filled circles) with non-transgenic Langdon durum homoeologous translocation line '685' F3:4 plants as male. Lines indicate suggested delineations in kernel texture phenotypic classes.
Figure 12:
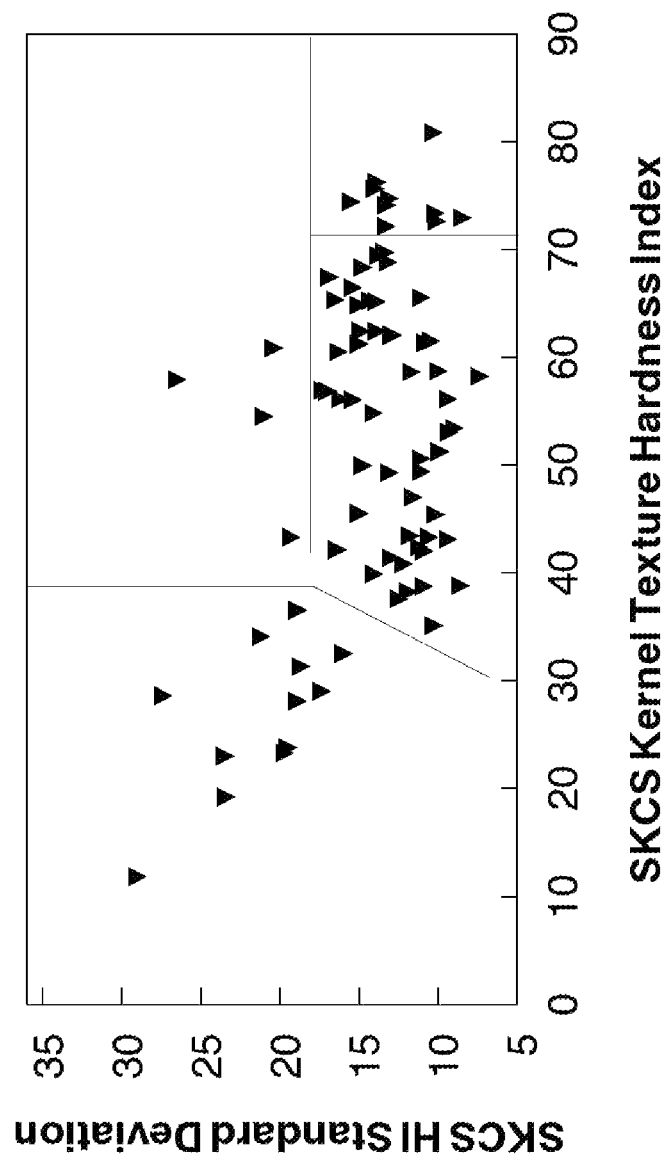
FIG. 12. Plot of SKCS kernel texture Hardness Index (HI) versus SKCS HI standard deviation of F2 kernels harvested from individual F1 plants derived by crossing the Italian durum wheat cultivar Svevo (filled triangles) with non-transgenic Langdon durum homoeologous translocation line '688' F3:4 plants as male. Lines indicate suggested delineations in kernel texture phenotypic classes.
Figure 13:
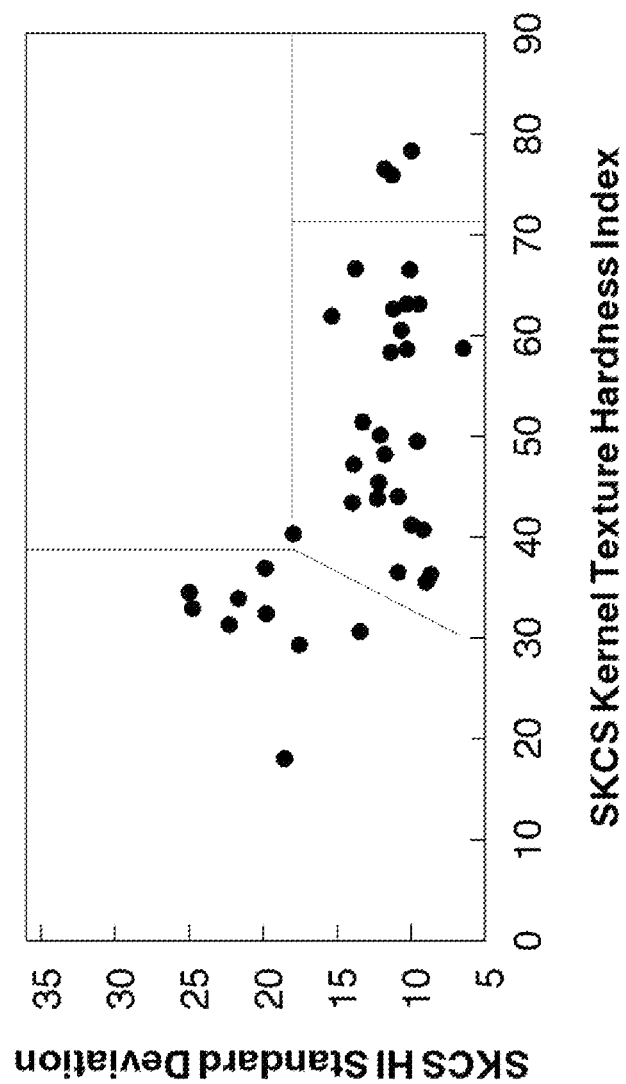
FIG. 13. Plot of SKCS kernel texture Hardness Index (HI) versus SKCS HI standard deviation of F2 kernels harvested from individual F1 plants derived by crossing the Italian durum wheat cultivar Creso (filled circles) with non-transgenic Langdon durum homoeologous translocation line '688' F3:4 plants as male. Lines indicate suggested delineations in kernel texture phenotypic classes.

Langdon durum homoeologous putative translocation line 674 was crossed to Svevo durum cultivar and produced progeny with SKCS kernel texture from 5 to 80 (FIG. 2). 80 (FIG. 2). Segregation was unpredictable and highly chaotic but recovery of soft progeny indicated that line 674 possessed a homoeologous translocation bearing the Hardness locus. Phenotypic segregation was not predictable and did not conform to any expected genetic ratio, indicating potential genome instability.

Langdon durum homoeologous translocation line 674 was crossed to Creso durum cultivar and produced progeny with SKCS kernel texture from 22 to 83 (FIG. 3); phenotypic segregation was not predictable and did not conform to any expected genetic ratio, indicating potential genome instability.

Langdon durum homoeologous translocation line 675 was crossed to Svevo durum cultivar and produced progeny with SKCS kernel texture from 17 to 82 (FIG. 4); phenotypic segregation was not predictable and did not conform to any expected genetic ratio, indicating potential genome instability.

Langdon durum homoeologous translocation line 675 was crossed to Creso durum cultivar and produced progeny with SKCS kernel texture from 38 to 57 (FIG. 5); phenotypic segregation was not predictable and did not conform to any expected genetic ratio, indicating potential genome instability.

Langdon durum homoeologous translocation line 678 was crossed to Svevo durum cultivar and produced progeny with SKCS kernel texture from 27 to 76 (FIG. 6); phenotypic segregation was not predictable and did not conform to any expected genetic ratio, indicating potential genome instability.

Langdon durum homoeologous translocation line 678 was crossed to Creso durum cultivar and produced progeny with SKCS kernel texture from 23 to 63 (FIG. 7); phenotypic segregation was not predictable and did not conform to any expected genetic ratio, indicating potential genome instability.

Langdon durum homoeologous translocation line 679 was crossed to Svevo durum cultivar and produced progeny with SKCS kernel texture from 57 to 77 (FIG. 8); phenotypic segregation was not predictable and did not conform to any expected genetic ratio, indicating potential genome instability.

Langdon durum homoeologous translocation line 679 was crossed to Creso durum cultivar and produced progeny with SKCS kernel texture from 50 to 80 (FIG. 9); phenotypic segregation was not predictable and did not conform to any expected genetic ratio, indicating potential genome instability.

Langdon durum homoeologous translocation line 685 was crossed to Svevo durum cultivar and produced progeny with SKCS kernel texture from 28 to 63 (FIG. 10); phenotypic segregation was not predictable and did not conform to any expected genetic ratio, indicating potential genome instability.

Langdon durum homoeologous translocation line 685 was crossed to Creso durum cultivar and produced progeny with SKCS kernel texture from 22 to 82 (FIG. 11); phenotypic segregation was not predictable and did not conform to any expected genetic ratio, indicating potential genome instability.

Langdon durum homoeologous translocation line 688 was crossed to Svevo durum cultivar and produced progeny with SKCS kernel texture from 12 to 81 (FIG. 12); phenotypic segregation was not predictable and did not conform to any expected genetic ratio, indicating potential genome instability.

Langdon durum homoeologous translocation line 688 was crossed to Creso durum cultivar and produced progeny with SKCS kernel texture from 18 to 78 (FIG. 13); phenotypic segregation was not predictable and did not conform to any expected genetic ratio, indicating potential genome instability.

As demonstrated above, all six Langdon durum homoeologous translocation lines that were produced as disclosed in steps 1-9 of this example comprised the homoeologous translocation carrying the Hardness gene locus, in either the homozygous or heterozygous condition. Also clear is that all the lines were segregating and/or were unstable i.e., did not behave as diploids in meiosis. As will be demonstrated hereinbelow, the translocations were crossed, selected and stabilized to provide non-transgenic durum wheat plants having grain with soft kernel texture.

Seeds from each of 10 plants from each of lines 678 and 683 were bulked and subjected to SKCS kernel texture analysis. Results showed them to be highly heterogeneous for kernel texture. Mean hardness index and standard deviation were 34±31 and 41±33, line 678 and 683, respectively. The SKCS also produces a four-class histogram with hardness index limits of ≦33, 34-46, 47-59, and ≧60. For line 678 the percentages of kernels in each class were 59, 5, 6 and 30, and for line 683 the percentages were 48, 7, 7 and 38. These data clearly indicated that as a population, the kernel texture distributions for both lines were highly bimodal with about half the kernels markedly soft (i.e. Hardness Index ≦33).

Figure 14:
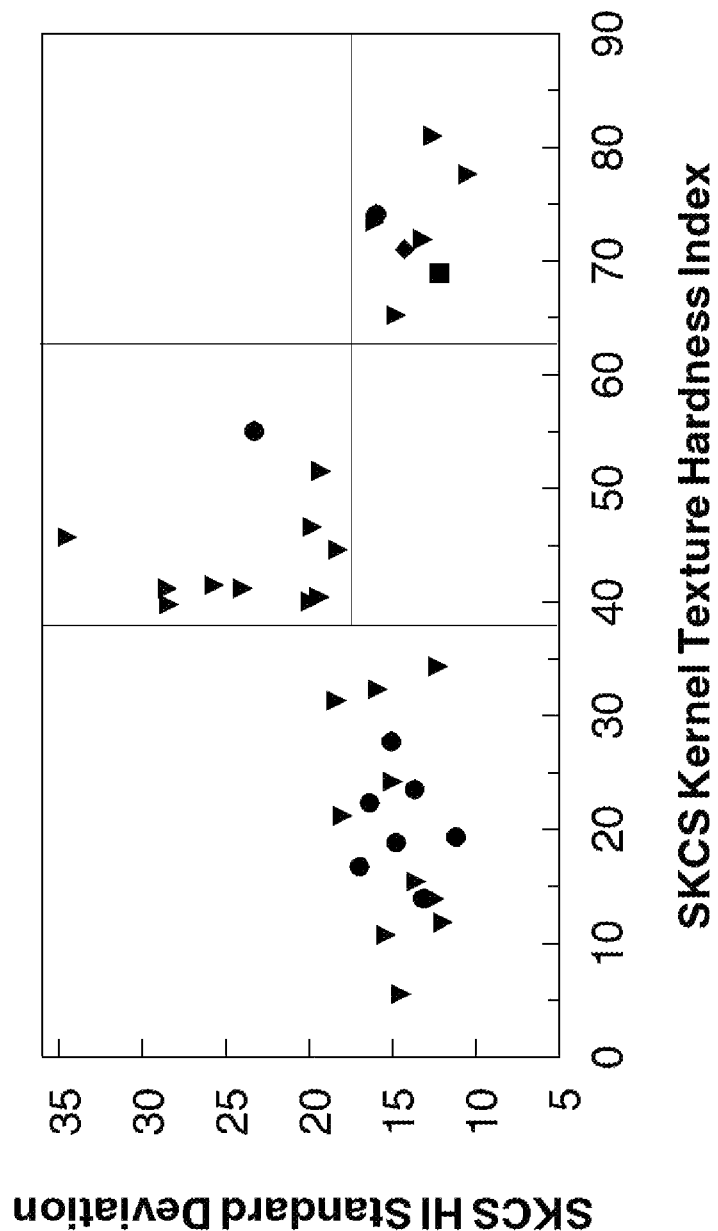
FIG. 14. Plot of SKCS kernel texture Hardness Index (HI) versus SKCS HI standard deviation of F5 kernels harvested from individual F4 plants derived by self pollinating three different non-transgenic Langdon durum homoeologous translocation lines crossed to the Italian durum wheat cultivar Creso (filled circles) and Svevo (filled triangles). Creso (filled square) and Svevo (filled diamond) parents are shown. Lines indicate suggested delineations in kernel texture phenotype classes.

F2 seeds from a small sub-sample of the F1 plants of the crosses Creso/685 and Creso/688 described above were grown, self fertilized and assayed for SKCS kernel texture. One plant each of crosses Creso/685 and Creso/688 produced Hardness Index and standard deviation of 69±24 and 29±8, respectively. Five plants from the Svevo/675 cross produced hardness index and standard deviation of 38±10, 56±19, 32±18, 22±20 and 19±20. One to five F3 plants from each line were grown to maturity, harvested and the seed used to plant F3:4 rows at the Washington State University Spillman Agronomy Farm, Pullman, Wash. Thirty-four rows in total were harvested and the F5 seed assayed for SKCS kernel texture (FIG. 14). The distribution of kernel texture phenotype was in keeping with a single locus-two allele model wherein those lines with hardness index greater than 65 and standard deviation less than 16 putatively lacked the Hardness-containing translocation and were uniformly hard, those with hardness index from about 40 to 65 and standard deviation greater than 18.3 were putatively heterogeneous, and those with hardness index less than 35 were soft and putatively carried the Hardness-containing translocation. In this group of soft wheat lines, the standard deviation ranged from 11.2-18.4. The two durum parents, Creso and Svevo, were located in the 'hard' group.

As disclosed below, crosses between Langdon durum homoeologous translocation line 674 and Svevo were conducted to provide a non-transgenic soft durum wheat variety referred to herein as Soft Svevo durum wheat WAS 080240001, representative seed of such line having been deposited under ATCC Accession No. PTA-10087.

Line 152 was selected from the cross between Langdon durum homoeologous translocation line 674 and Svevo (see FIG. 2). Although one line was selected other soft kernel progeny from this cross as well as progeny from any and all other crosses would have been expected to produced similar results. This particular line was selected as it exhibited the overall softest kernel texture and therefore was expected to produce soft progeny with stable soft kernel inheritance. DNA was extracted from distal half seeds (n=10) and assayed using PCR and puroindoline a and b primers. To amplify puroindoline-a gene(s) the sense-strand primer was 5'-ATGAAGGCCCTCTTCCTCA-3' (SEQ ID NO: 1) and the antisense-strand primer was 5'-TCACCAGTAATAGCCAAT-AGTG-3' (SEQ ID NO:2). To amplify puroindoline-b gene(s) the sense-strand primer was 5'-ATGAAGACCTTATTCCTC-CTA-3' (SEQ ID NO:3) and the antisense-strand primer was 5'-TCACCAGTAATAGCCACTAGGGAA-3' (SEQ ID NO:4). PCR was carried out by known methods (see e.g., Sambrook and Russell (2001) Molecular Cloning, A Laboratory Manual, CSH Press).

Figure 15:
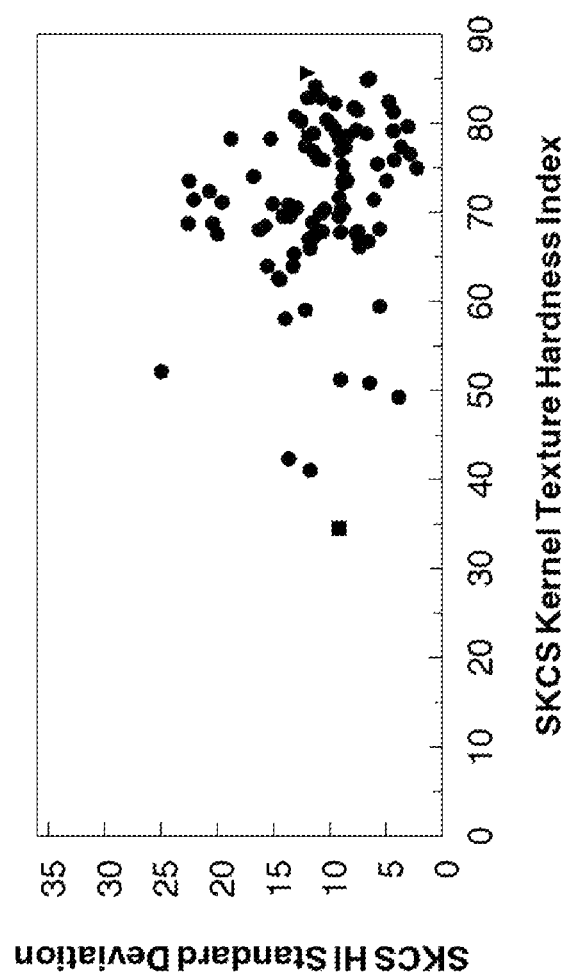
FIG. 15. Plot of SKCS kernel texture Hardness Index (HI) versus SKCS HI standard deviation of BC3F2 kernels harvested from individual BC3F1 plants derived from Svevo/674 line no. 152 (filled circles and the filled square). The selected progeny (filled square is Soft Svevo durum wheat WAS 080240001, representative seed of such line having been deposited under ATCC Accession No. PTA-10087) is shown as are two Svevo (filled triangle) parent plants.

Six of the ten seeds were positive for both puroindoline a and b. The remaining embryo half of these seeds were germinated and the plants grown, emasculated and used for crossing to Svevo (as female) (representing back-cross 1, BC1). Resultant progeny were assayed for puroindoline genes via PCR as before (ten of 19 seeds were positive for both genes). PCR-positive individual seeds were propagated and used for BC2. The process was repeated for BC3. Puroindoline PCR-positive progeny were grown in the field near Viterbo, Italy, and allowed to self pollinate. Four to seven BC3F2 seeds from each of these BC3F1 plants were subjected to SKCS kernel texture analysis on an individual plant basis (FIG. 15). A total of 92 plants were evaluated along with two plants of Svevo. From these results, a single plant (identified as no. 88) was selected as having a high probability of being uniformly soft and carrying the Hardness translocation. This selection was advanced through two more cycles of self pollination to produce BC3F4 seed.

A 500-gram aliquot of BC3F4 seed of line no. 88 was provided to Dr. Kim Shantz, WestBred LLC, Yuma, Ariz., for field increase during the 2007-2008 crop season. Approximately 135 kg of BC3F5 seed was harvested in 2008. The kernel texture of this field increase was hardness index 24±14, indicating that it was uniformly soft. Dr. Shantz, described line no. 88 as being uniform and otherwise indistinguishable from Svevo. Line no. 88 was herein designated Soft Svevo durum wheat WAS 080240001, representative seed from this Arizona production having been deposited under ATCC Accession No. PTA-10087.

Example 2

Deposit Information

Representative of, but not limiting the invention, Applicants have deposited seeds from Soft Svevo durum wheat WAS 080240001, with the American Type Culture Collection.

Applicants have made available to the public without restriction a deposit of at least 2500 seeds of a non-transgenic tetraploid wheat plant having soft textured endosperm i.e., Soft Svevo durum wheat WAS 080240001, with the American Type Culture Collection (ATCC), Rockville, Md. 20852. The deposit was made May 27, 2009, under ATCC Accession No. PTA-10087.

The deposit will be maintained in the ATCC depository, which is a public depository, for a period of 30 years, or 5 years after the most recent request, or for the effective life of the patent, whichever is longer, and will be replaced if a deposit becomes nonviable during that period.

Example 3

Figure 16:
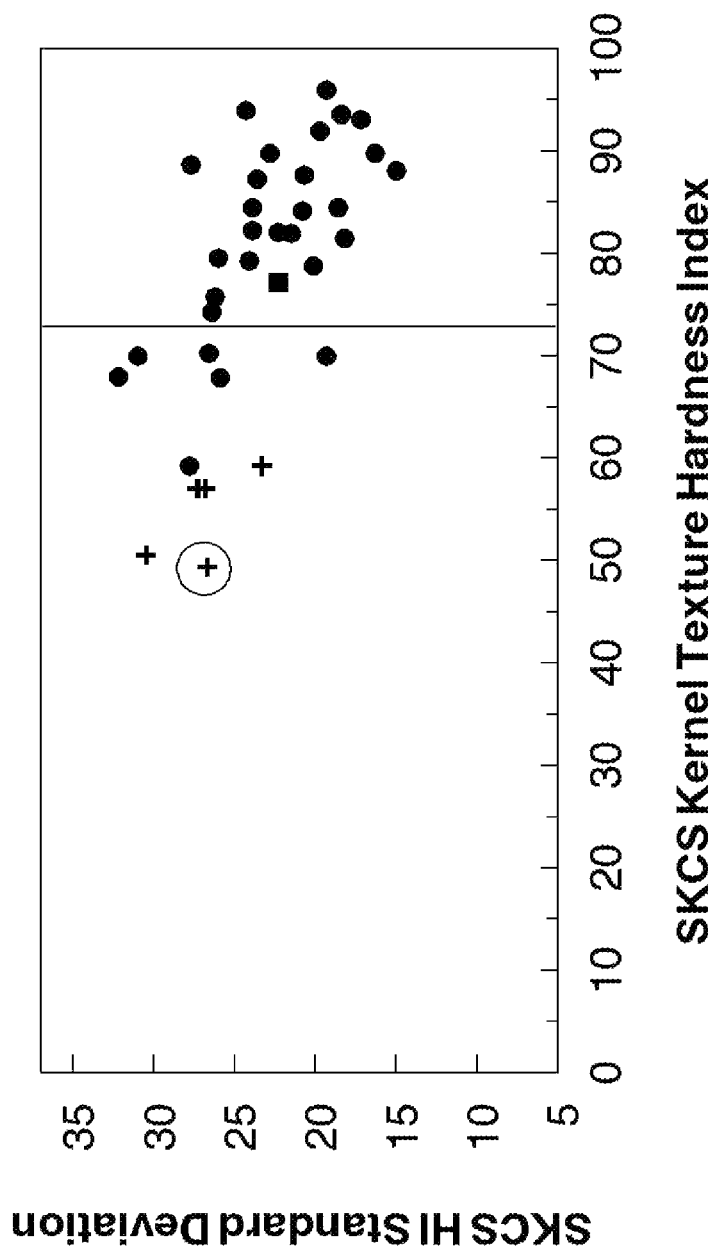
FIG. 16. Plot of SKCS kernel texture Hardness Index (HI) versus SKCS HI standard deviation of F2 kernels harvested from individual F1 plants derived by crossing the North American durum wheat cultivar Kyle with non-transgenic Langdon durum homoeologous translocation line 678 plants as male (filled circles). Kyle (filled square) parent plant is shown. The line indicates a suggested delineation in kernel texture phenotype classes. The circled progeny line was used in segregation analysis shown in FIG. 18. The cross symbol identifies the five lines selected for back-crossing to Kyle (two from 678 cross, three from 683 cross).

The following example illustrates use of the non-transgenic putative soft kernel Langdon durum homoeologous translocation line 678 in a cross to Kyle durum cultivar and the production of progeny with SKCS kernel texture from 49 to 96 (FIG. 16). The non-transgenic putative soft kernel Langdon durum homoeologous translocation line 683 was crossed to Kyle durum cultivar and produced progeny with SKCS kernel texture from 48 to 95 (FIG. 17).

One F1 plant of the pedigree Kyle/683 with a hardness index of 49±27 (identified in FIGS. 6 and 17) was selected, grown, and its progeny tested for kernel texture segregation. Nineteen F2 plants were grown to maturity, harvested, and the F3 kernels subjected to SKCS kernel texture analysis (FIG. 18). Most F2 lines could be classified based on kernel texture phenotype: one line was soft with a hardness index of 16±17, and 3-5 lines were hard with hardness indexes greater than 81. However, three of these had relatively low standard deviations (<17) whereas the other two had high standard deviations (>21). The remainder had hardness indexes from 47 to 70; all but one had standard deviations greater than 22. The segregation ratio indicated that the soft class may have been under-represented.

Figure 17:
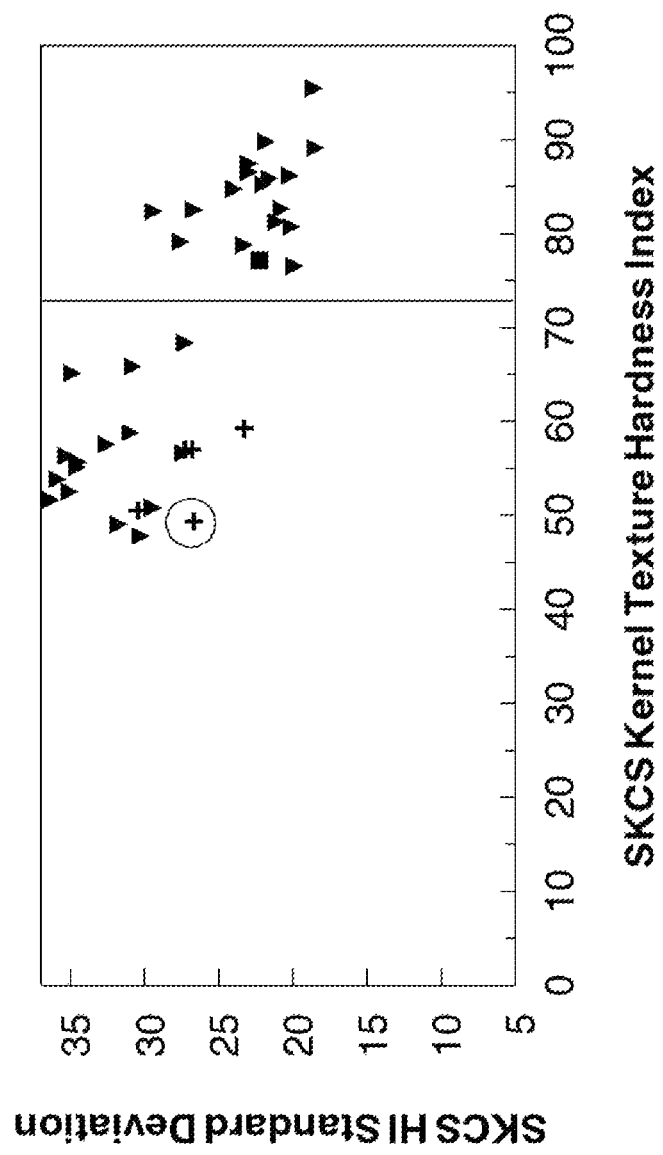
FIG. 17. Plot of SKCS kernel texture Hardness Index (HI) versus SKCS HI standard deviation of F2 kernels harvested from individual F1 plants derived by crossing the North American durum wheat cultivar Kyle with non-transgenic Langdon durum homoeologous translocation line 683 plants as male (filled triangles). Kyle (filled square) parent plant is shown. The line indicates a suggested delineation in kernel texture phenotype classes. The circled progeny line was used in segregation analysis shown in FIG. 18. The cross symbol identifies the five lines selected for back-crossing to Kyle (two from 678 cross, three from 683 cross).
Figure 18:
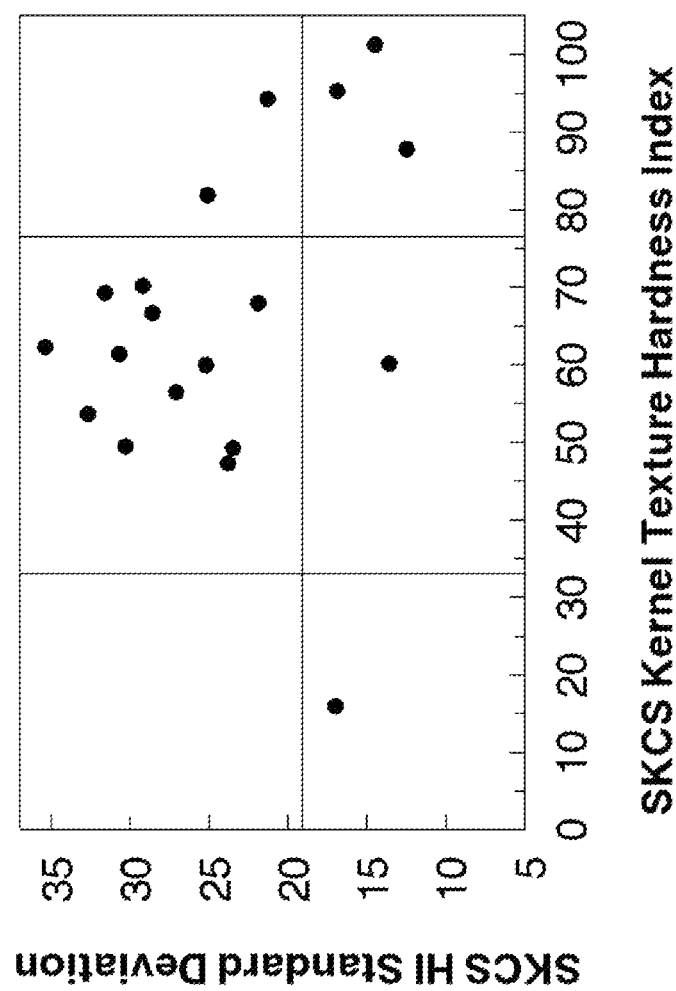
FIG. 18. Plot of SKCS kernel texture Hardness Index (HI) versus SKCS HI standard deviation of F3 kernels harvested from individual F2 plants derived from a single F1 plant, and produced by crossing the North American durum wheat cultivar Kyle with non-transgenic Langdon durum homoeologous translocation line 683. The lines indicate suggested delineations in kernel texture phenotype classes.
Figure 19:
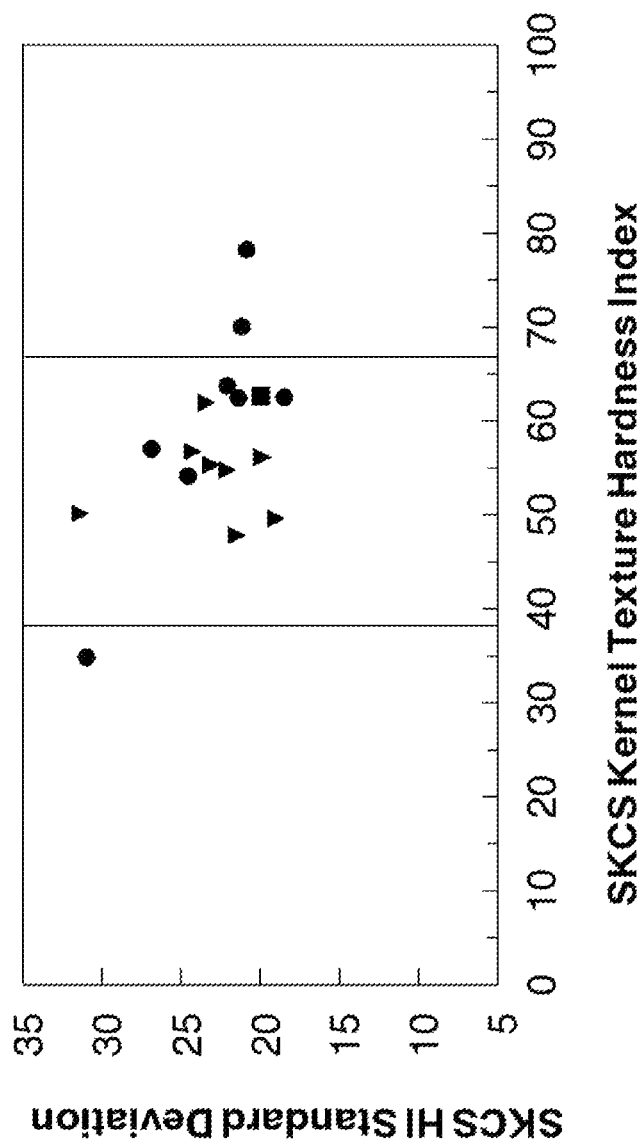
FIG. 19. Plot of SKCS kernel texture Hardness Index (HI) versus SKCS HI standard deviation of BC1F2 kernels harvested from individual BC1F1 plants derived by crossing the North American durum wheat cultivar Kyle with non-transgenic Langdon durum homoeologous translocation line 678 (filled circles) and 683 (filled triangles). Kyle (filled square) parent plant is shown. The lines indicate suggested delineations in kernel texture phenotype classes.

Two F2 plants of the cross Kyle/678 (those with hardness indexes of 57±27 and 59±23) and three of the cross Kyle/683 (those with hardness indexes of 49±27, 51±31 and 57±27) were selected and advanced (identified in FIGS. 16 and 17). F2 plants were grown and back-crossed to Kyle. BC1F1 plants were grown in a glasshouse, harvested and the seed from eight plants from each cross was subjected to SKCS kernel texture analysis (FIG. 19). Mean hardness index ranged from 35 to 78, and all plants had hardness index standard deviation of 19 or greater. Progeny resulting from the Kyle/678 cross were more variable in hardness index than were those from Kyle/683. A soft line was clearly recovered from the Kyle/678 cross (hardness index 35). Setting delineations at about 37 and 67 hardness index, the progeny of Kyle/678 approximated a 1:2:1 segregation ratio, whereas the progeny of the Kyle/683 cross all fell into the intermediate class of kernel texture.

Example 4

The following example illustrates the use of the non-transgenic Soft Svevo durum wheat WAS 080240001, representative seed having been deposited under ATCC Accession No. PTA-10087, was used as a parent to produce a non-transgenic soft textured durum wheat grain cultivar.

Figure 20:
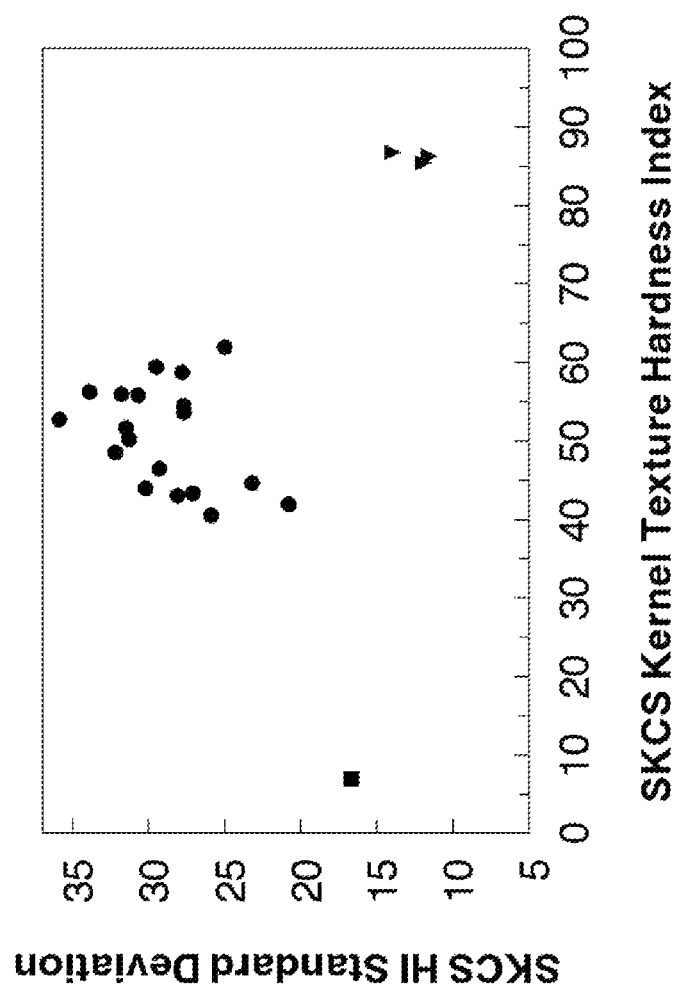
FIG. 20. Plot of SKCS kernel texture Hardness Index (HI) versus SKCS HI standard deviation of F2 kernels harvested from individual F1 plants derived by crossing the North American durum wheat cultivar Havasu with non-transgenic Soft Svevo durum wheat WAS 080240001 (filled circles). Havasu (filled triangles) parent plants are shown, and a soft hexaploid wheat control (filled square).

BC3F4 plants of Soft Svevo durum wheat WAS 080240001 were grown as pollen donor for crossing to Havasu durum wheat cultivar (female). F1 seed was harvested and nineteen F1 plants were grown to maturity, harvested and the seed subjected to SKCS kernel texture analysis (FIG. 20). The results were consistent with a single gene, bi-allelic segregation model with a mid-range of kernel texture from hardness index of 41 to 62, all with standard deviations greater than 21. Inspection of the SKCS four-class histogram results showed strong bi-modality for all F1 plants where the greatest proportion of kernels of each line were in the #33 and ∃60 classes consistent with normal F2 segregation within each spike. Seven F1 plants were selected and about five F2 plants of each were grown and crossed "blind" to Havasu. About half the crosses were successful; non-emasculated F2 spikes were allowed to self pollinate to produce F3 seeds. These F3 seeds were used as a 'progeny test' to evaluate the genotype of the parental F2 plants.

Figure 21:
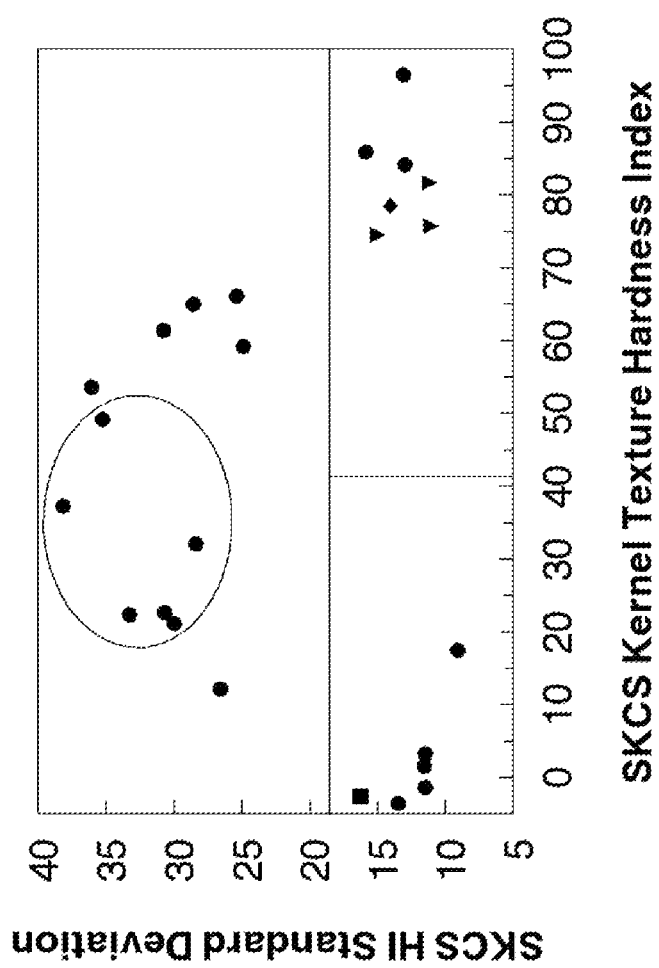
FIG. 21. Plot of SKCS kernel texture Hardness Index (HI) versus SKCS HI standard deviation of F3 kernels harvested from individual F2 plants derived by crossing the North American durum wheat cultivar Havasu with non-transgenic Soft Svevo durum wheat WAS 080240001 (filled circles). Havasu (filled triangles) parent plants are shown, as is a soft (filled square) and hard (filled diamond) hexaploid wheat controls. The lines indicate suggested delineations in kernel texture phenotype classes. BC1 seeds were selected from those plants that are circled for advancing.

The F2 plants showed a characteristic normal one gene locus segregation, wherein a distinct three-cluster pattern was observed: a group of low (soft) hardness index with standard deviation less than 14, a group of high (hard) hardness index with standard deviation less than 16, and an intermediate hardness index group with hardness index standard deviation greater than 25 indicating 'mixed' (segregating) kernel texture alleles (FIG. 21). The observed segregation ratio was 5 soft:12 intermediate:3 hard. In this trial, soft durum lines were especially soft with the lowest value equal to −4.

Figure 22:
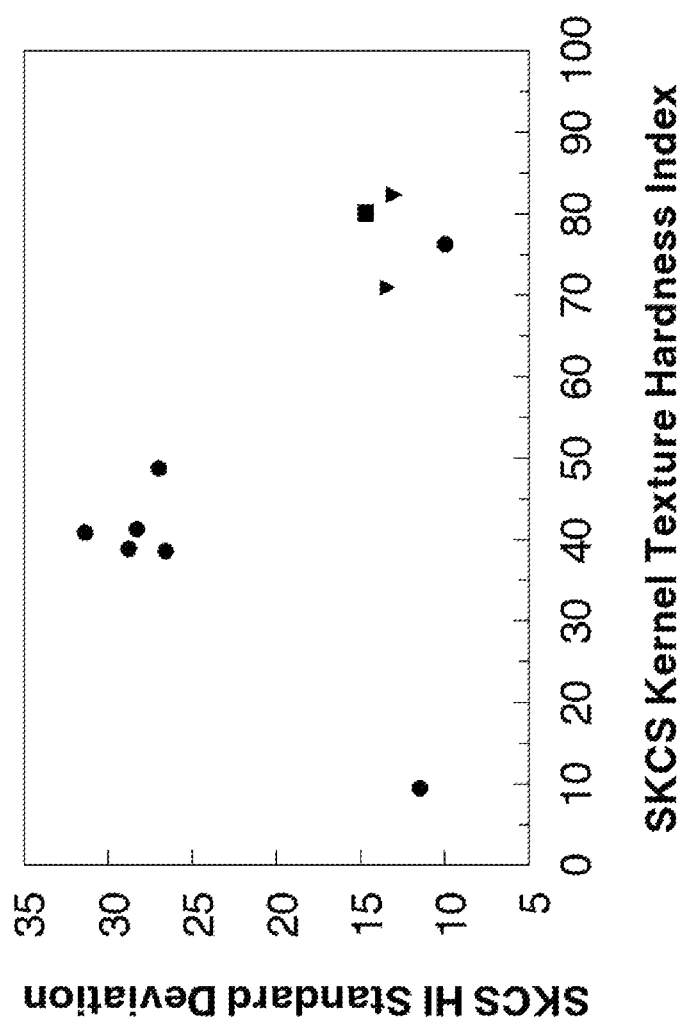
FIG. 22. Plot of SKCS kernel texture Hardness Index (HI) versus SKCS HI standard deviation of BC1F3 kernels harvested from individual BC1F2 plants derived by crossing the North American durum wheat cultivar Havasu with non-transgenic Soft Svevo durum wheat WAS 080240001 (filled circles). Havasu (filled triangles) parent plants are shown, as is a hard hexaploid wheat control (filled square).

BC1 seeds were selected from six F2 plants with hardness index from 21 to 49 and standard deviation greater than 28, indicating that they were heterozygous for the Hardness containing—translocation. Seven of these BC1F1 plants were again back-crossed blind to Havasu for BC2. As before, the 'remnant' F2 seeds from the self pollinated spikes were subjected to SKCS kernel texture analysis on a BC1F1 plant basis (FIG. 22). Two plants did not fit the expected model, that is, one was soft (hardness index 9±12) and one was hard (hardness index 76±10). The other five were advanced.

Figure 23:
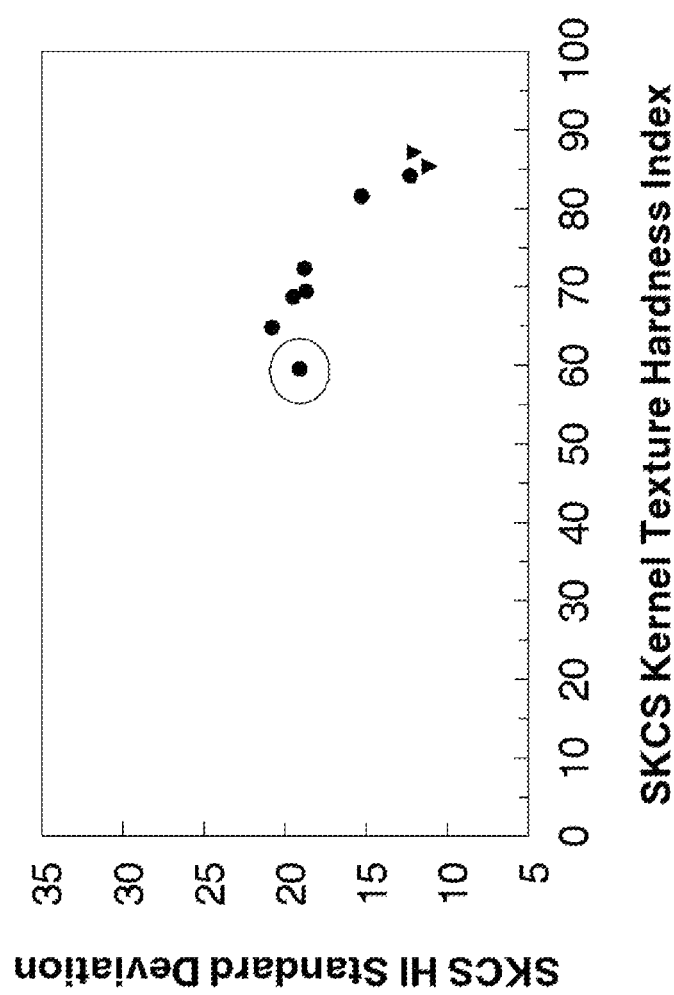
FIG. 23. Plot of SKCS kernel texture Hardness Index (HI) versus SKCS HI standard deviation of BC2F3 kernels harvested from individual BC2F2 plants derived by crossing the North American durum wheat cultivar Havasu with non-transgenic Soft Svevo durum wheat WAS 080240001 (filled circles). Havasu (filled triangles) parent plants are shown. BC3F1 seeds were selected from the plant that is circled for advancing.

Seven BC2F1 plants were grown, emasculated and back-crossed blind to Havasu, as before, for BC3. The remnant BC2F2 kernels were assayed for kernel texture (FIG. 23). Four of the seven showed a broader distribution (4-class histogram), whereas the other three appeared to be uniformly hard. BC3F1 seeds were selected from the softest plant (identified in FIG. 23) and advanced.

Figure 24:
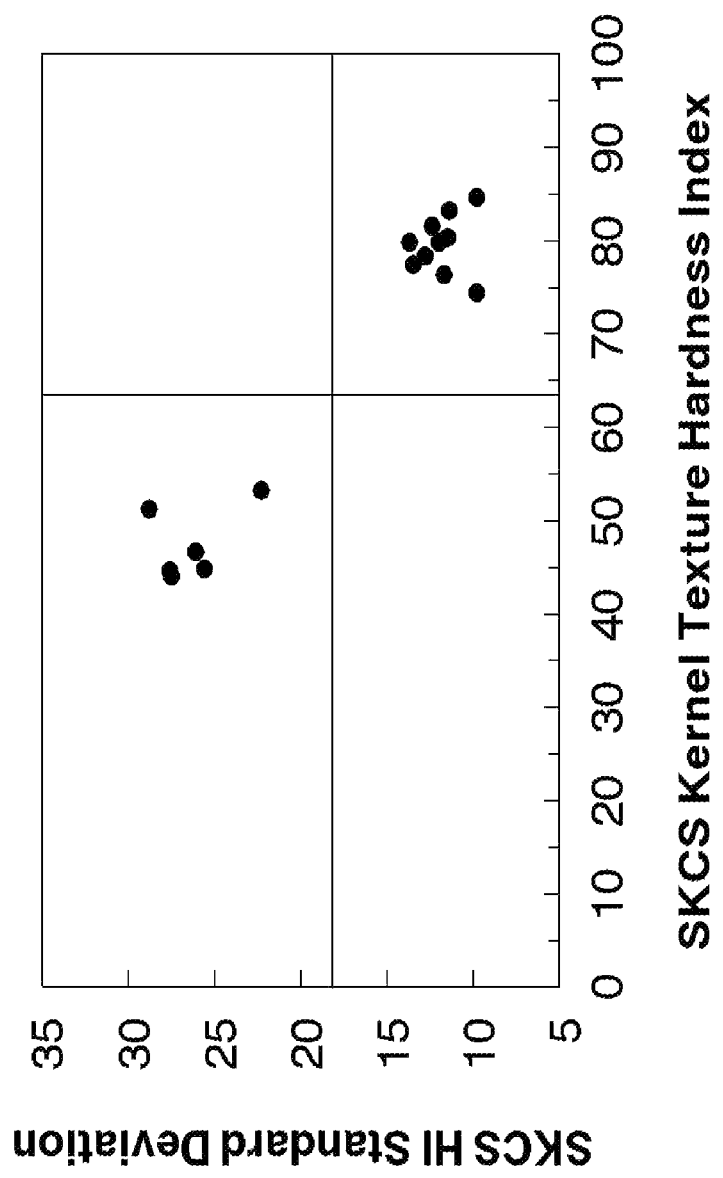
FIG. 24. Plot of SKCS kernel texture Hardness Index (HI) versus SKCS HI standard deviation of BC3F2 kernels harvested from individual BC3F1 plants derived by crossing the North American durum wheat cultivar Havasu with non-transgenic Soft Svevo durum wheat WAS 080240001. The lines indicate suggested delineations in kernel texture phenotype classes.

Sixteen BC3F1 plants were grown to maturity, harvested and subjected to kernel texture analysis (FIG. 24). The results showed a clear bimodal distribution of BC3F1 plants wherein one group was comprised of BC3F1 plants carrying no Hardness-containing translocation, and the other derived from 'soft' and 'hard' kernel heterozygotes (resulting from segregation within the spike). The observed frequency was 6 heterozygous: 10 hard.

In yet a further illustration, the following example illustrates the use of the non-transgenic Soft Svevo durum wheat WAS 080240001 as a parent to produce a non-transgenic soft textured durum wheat grain cultivar.

Figure 25:
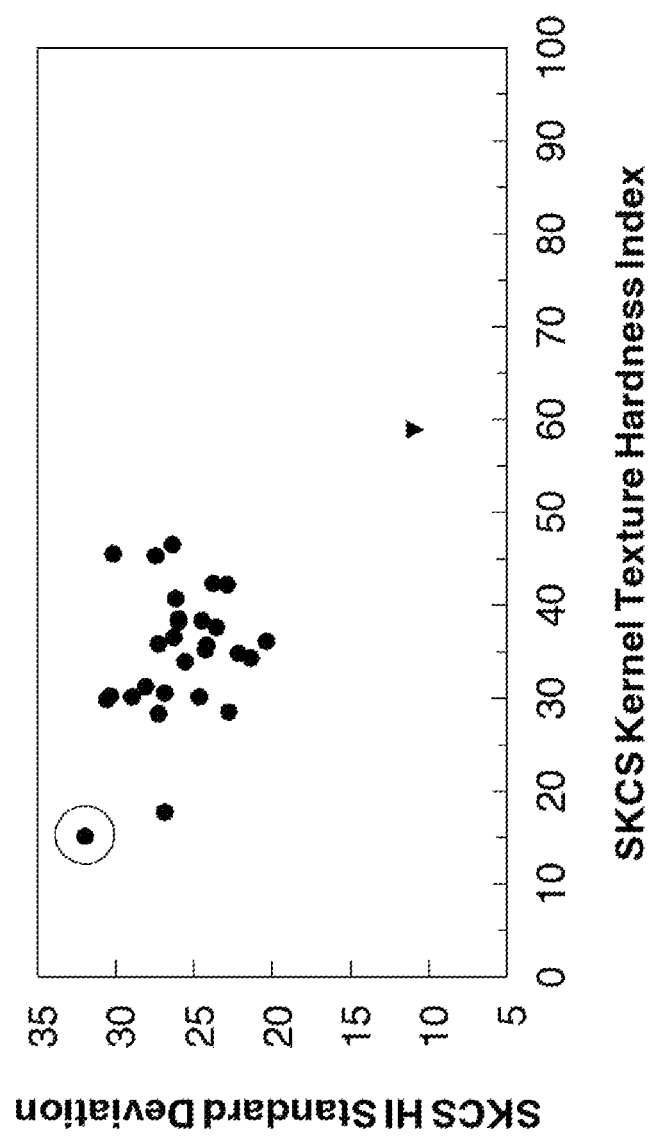
FIG. 25. Plot of SKCS kernel texture Hardness Index (HI) versus SKCS HI standard deviation of F2 kernels harvested from individual F1 plants derived by crossing the North American durum wheat experimental breeding line CA801-721 with non-transgenic Soft Svevo durum wheat WAS 080240001 (filled circles). CA801-721 (filled triangle) parent plant is shown. F2 seeds were selected from the plant that is circled for advancing.

Plants of Soft Svevo durum wheat WAS 080240001 were grown as pollen donor for crossing to experimental durum wheat breeding line CA801-721 (female). F1 seed was harvested and 28 F1 plants were grown to maturity, harvested and the seed subjected to SKCS kernel texture analysis (FIG. 25).

Figure 26:
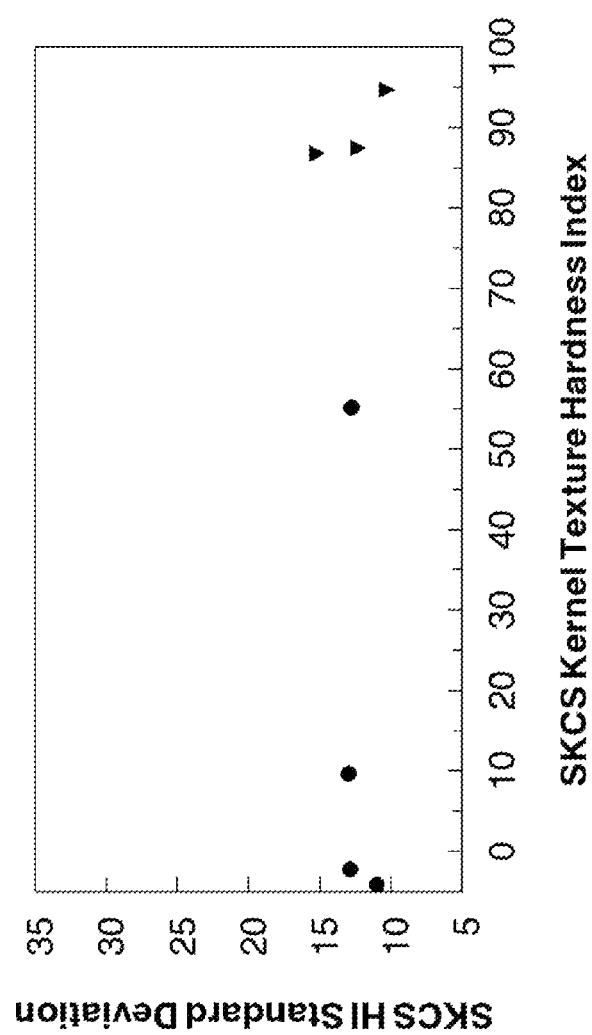
FIG. 26. Plot of SKCS kernel texture Hardness Index (HI) versus SKCS HI standard deviation of F2 kernels harvested from individual F1 plants derived by crossing the North American durum wheat experimental breeding line CA801-721 with non-transgenic Soft Svevo durum wheat WAS 080240001 (filled circles). CA801-721 (filled triangles) parent plants are shown.
Figure 27:
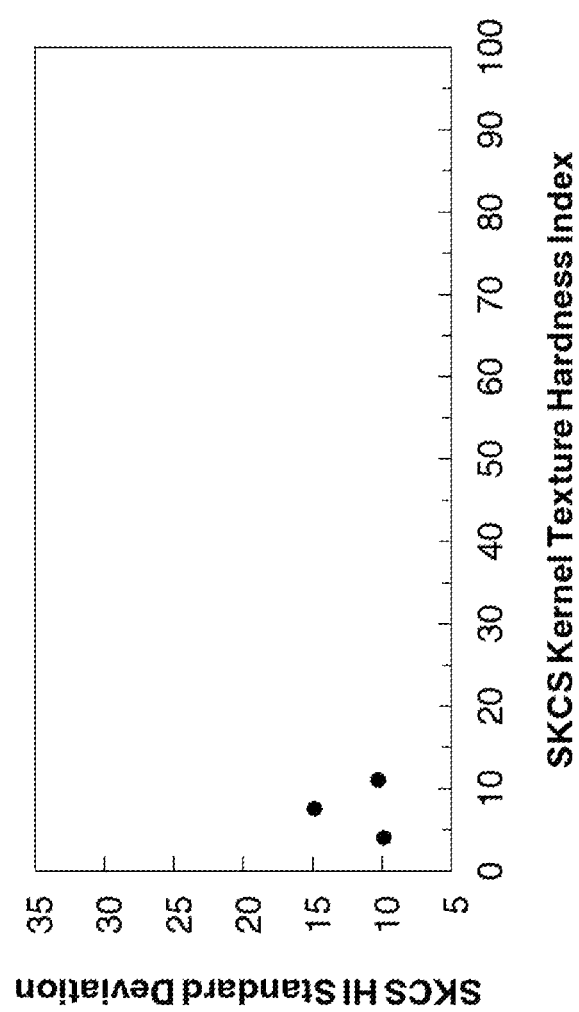
FIG. 27. Plot of SKCS kernel texture Hardness Index (HI) versus SKCS HI standard deviation of F2 kernels harvested from individual F1 plants derived by crossing the North American durum wheat experimental breeding line CA801-721 with non-transgenic Soft Svevo durum wheat WAS 080240001.

The softest plant was selected (see FIG. 25), F2 seed was used to produce F2 plants, four of which were harvested and subjected to SKCS kernel texture analysis (FIG. 26). The three softest plants with SKCS kernel texture less than 10 were selected and used to produce F3 plants, the seed from which were subjected to SKCS kernel texture analysis (FIG. 27). The result indicated clearly that the soft kernel trait was stable and inherited from the F2 to F3.

In yet another embodiment, the following example further illustrates use of the non-transgenic Soft Svevo durum wheat WAS 080240001 was used as a parent to produce a non-transgenic soft textured durum wheat grain cultivar.

Figure 28:
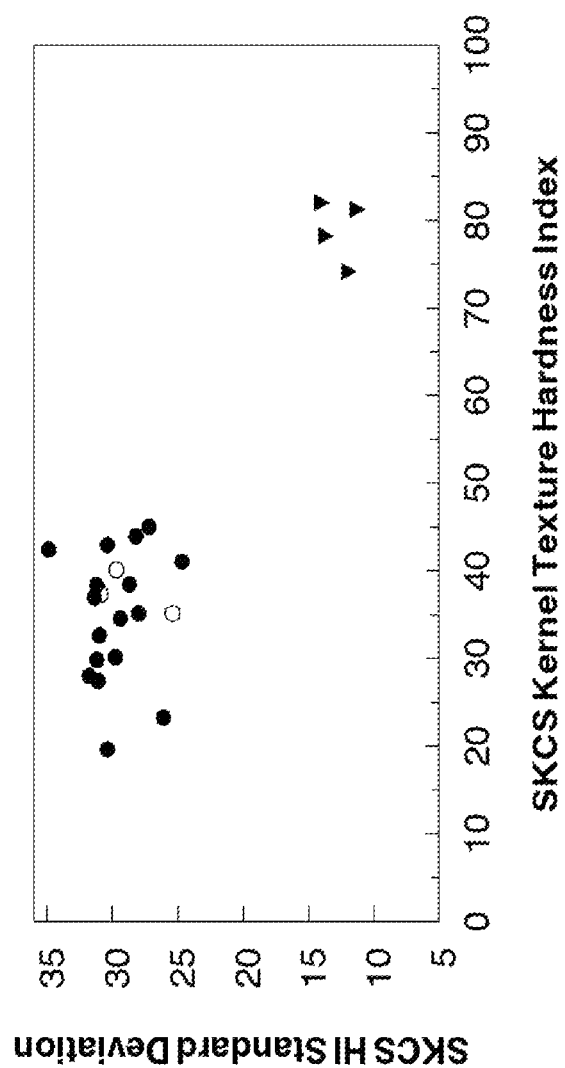
FIG. 28. Plot of SKCS kernel texture Hardness Index (HI) versus SKCS HI standard deviation of F2 kernels harvested from individual F1 plants derived by crossing the North American durum wheat cultivar Alzada with non-transgenic Soft Svevo durum wheat WAS 080240001. Alzada (filled triangles) parent plants are shown. The three plants represented by open circles were selected for advancing.

Plants of Soft Svevo durum wheat WAS 080240001 were grown as pollen donor for crossing to durum wheat cultivar Alzada (female). F1 seed was harvested and 20 F1 plants were grown to maturity, harvested and the seed subjected to SKCS kernel texture analysis (FIG. 28).

Figure 29:
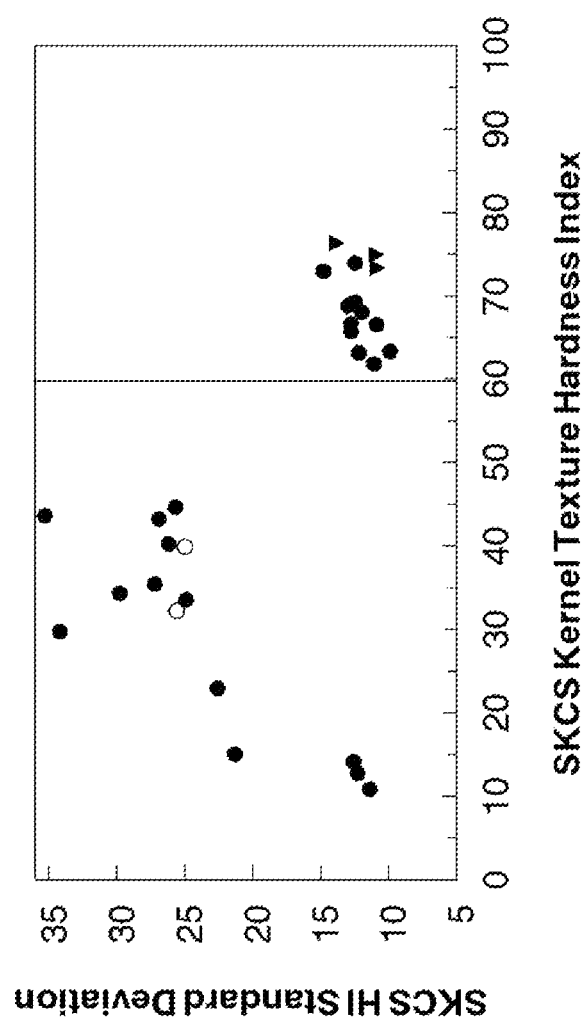
FIG. 29. Plot of SKCS kernel texture Hardness Index (HI) versus SKCS HI standard deviation of F3 kernels harvested from individual F2 plants derived by crossing the North American durum wheat cultivar Alzada with non-transgenic Soft Svevo durum wheat WAS 080240001. Alzada (filled triangles) parent plants are shown. BC1 seed from the two plants represented by open circles were selected for advancing.
Figure 30:
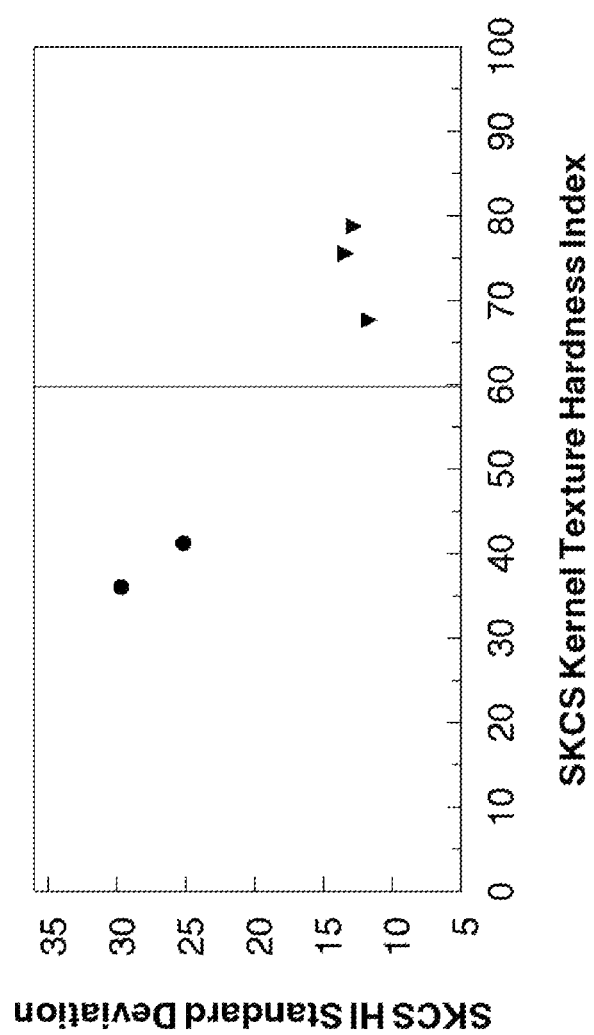
FIG. 30. Plot of SKCS kernel texture Hardness Index (HI) versus SKCS HI standard deviation of BC1F2 kernels harvested from individual BC1F1 plants derived by crossing the North American durum wheat cultivar Alzada with non-transgenic Soft Svevo durum wheat WAS 080240001. Alzada (filled triangles) parent plants are shown.

Three plants were selected (see FIG. 28), F2 seed was used to produce F2 plants some of which were emasculated and back-crossed blind to Alzada for BC1. The F3 kernels from each of 26 plants were harvested and subjected to SKCS kernel texture analysis (FIG. 29). BC1 seed from two plants (see FIG. 29) were selected; a number of plants were grown, but only two were subjected to SKCS kernel texture analysis (BC1F2 kernels) (FIG. 30), which indicated that both were likely segregating within the spike for Hardness. Both plants had been back-crossed blind to Alzada for BC2.

Figure 31:
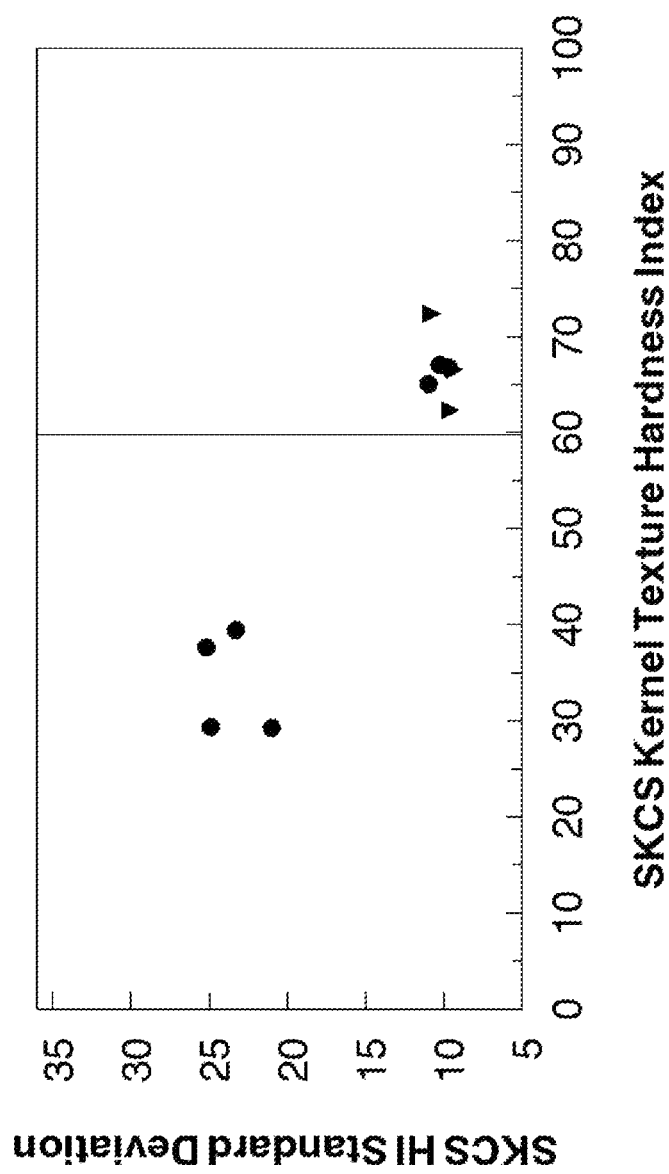
FIG. 31. Plot of SKCS kernel texture Hardness Index (HI) versus SKCS HI standard deviation of BC2F2 kernels harvested from individual BC2F1 plants derived by crossing the North American durum wheat cultivar Alzada with non-transgenic Soft Svevo durum wheat WAS 080240001. Alzada (filled triangles) parent plants are shown. BC3F1 kernels from the four plants with SKCS hardness indexes less than 45 were selected for advancing.

The BC2 kernels were harvested and grown as BC2F1 plants. These plants were emasculated and back-crossed blind to Alzada for BC3. Seven of the BC2F1 plants were subjected to SKCS kernel texture analysis (BC2F2 kernels) (FIG. 31). BC3F1 kernels from the four plants with SKCS hardness indexes less than 45 were selected for advancing.

In yet another embodiment, the following example illustrates further the use of the non-transgenic Soft Svevo durum wheat WAS 080240001 as a parent to produce a non-transgenic soft textured durum wheat grain cultivar.

Figure 32:
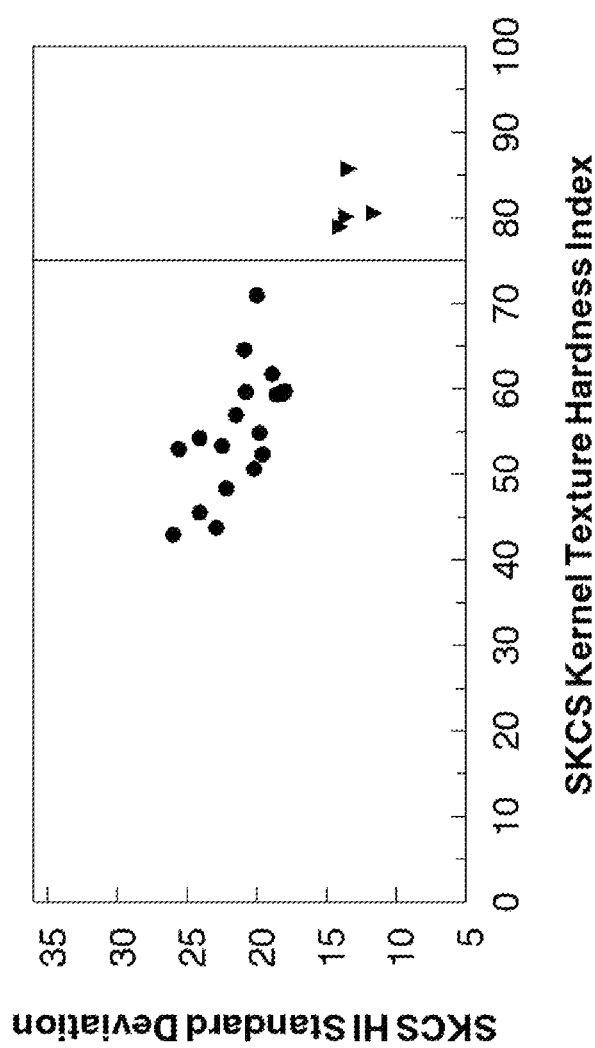
FIG. 32. Plot of SKCS kernel texture Hardness Index (HI) versus SKCS HI standard deviation of F2 kernels harvested from individual F1 plants derived by crossing the North American durum wheat cultivar Strongfield with non-transgenic Soft Svevo durum wheat WAS 080240001. Strongfield (filled triangles) parent plants are shown.

Plants of Soft Svevo durum wheat WAS 080240001 were grown as pollen donor for crossing to the durum wheat cultivar Strongfield (female). F1 seed was harvested and 18 F1 plants were grown to maturity, harvested and the seed subjected to SKCS kernel texture analysis (FIG. 32).

Figure 33:
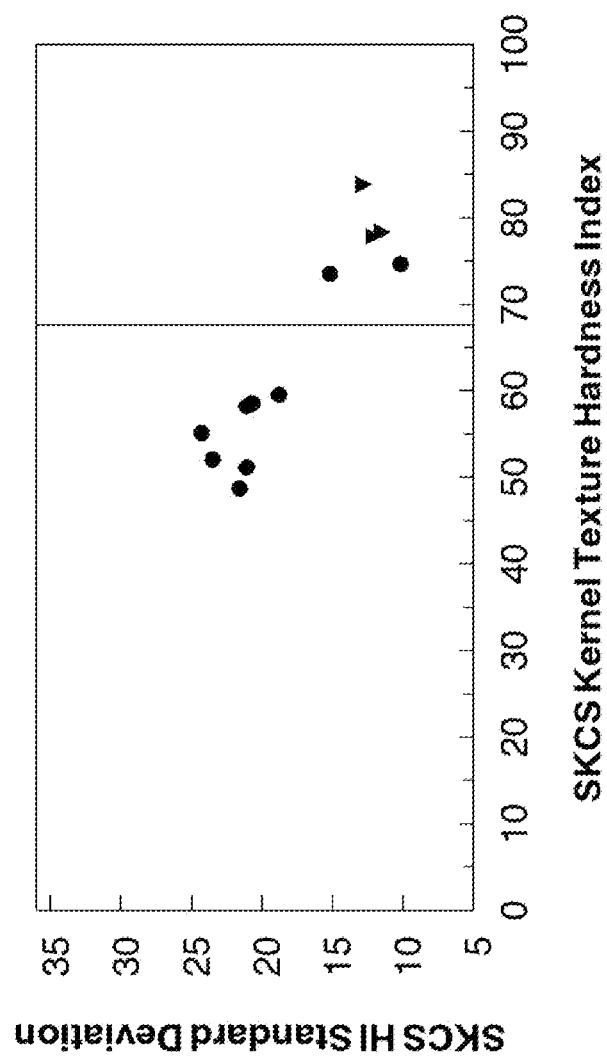
FIG. 33. Plot of SKCS kernel texture Hardness Index (HI) versus SKCS HI standard deviation of BC1F2 kernels harvested from individual BC1F1 plants derived by crossing the North American durum wheat cultivar Strongfield with non-transgenic Soft Svevo durum wheat WAS 080240001. Strongfield (filled triangles) parent plants are shown.

F2 seeds of two F1 plants were selected and grown, and used to back-cross blind to Strongfield. BC1F1 seeds were harvested and used to grow nine BC1F1 plants. The BC1F1 plants were harvested and their BC1F2 seeds subjected to SKCS kernel texture analysis (FIG. 33).

Example 5

The following example illustrates that milling of soft textured grain from the non-transgenic soft kernel durum wheat line.

Soft textured grain produced by a non-transgenic tetraploid wheat plant as disclosed herein (Soft Svevo), was milled on a Miag Multomat pilot-scale flour mill using only the first break rolls which were 10 inches diameter, 4 inches long, with a 'sharp' to 'dull' corrugation orientation, operating at 325 rpm with a 1:2.4 roll differential, an 8% spiral with 13.5 corrugations per inch, set to a gap of 70 mm, the grain was tempered to 14.5% moisture content for 24 hr, with an additional 0.5% temper added 30 minutes prior to milling, and milled at a feed rate of 786 grams per minute. Ground products were automatically sifted on two 720 micron and four 145 micron sieves that are part of the Miag mill and are operating at 240 rpm. The 'overs' from the 145 micron sieves was manually collected and resifted on a 150 micron sieve. Each of the various granulations was assayed for ash, protein and moisture contents.

With no additional work, effort, purifying or other means to increase yield or remove bran (thereby reducing ash content), the yield of granular product greater than 150 microns but less than 720 microns was 36.3% based on wheat to the mill, with an ash content of not more than 0.74%. As CFR §137.320 provides for up to 3% of semolina may pass through a 150 micron sieve, the total yield of semolina would equal not less than 37.3%. In contrast, Posner and Hibbs (1997, supra) indicate a break release for durum wheat as 9% and of hard wheat as 30%, whereas in the present embodiment, the break release for the soft durum was in excess of 55%.

In another exemplary embodiment, soft textured grain produced by a non-transgenic tetraploid wheat plant as disclosed herein (Soft Svevo), was milled on a Miag Multomat pilot-scale flour mill employing the complete mill flow, the mill rolls all being 10 inches diameter, 4 inches long and operating at 325 rpm with a 1:2.4 roll differential; the first break rolls had a 'sharp' to 'dull' corrugation orientation, an 8% spiral with 13.5 corrugations per inch, set to a gap of 70 mm; the second break rolls had a 'sharp' to 'dull' corrugation orientation, a 10% spiral with 19 corrugations per inch, set to a gap of 12 mm; the third break rolls had a 'sharp' to 'dull' corrugation orientation, a 10% spiral with 23.8 corrugations per inch, set to a gap of 3 mm; the first, second, third, fourth, and fifth midds rolls (reduction rolls) were smooth (no corrugations) and were set to 'contact' (no gap). The grain was tempered to 14.5% moisture content and held for 24 hr, with an additional 0.5% temper added 30 minutes prior to milling, and milled at a feed rate of 786 grams per minute. The movement of ground products was automatically and pneumatically conveyed throughout the mill; products were sifted and segregated as shown in FIG. 1. The sifter operated at 240 rpm. The results of that milling are presented in Table 1. The milling produced a yield of durum flour in excess of 80.9% at not more than 0.82% ash.

TABLE 1

| Stream | Yield % | Ash % | Cumulative Yield % | Cumulative Ash % |
| --- | --- | --- | --- | --- |
| First Midds | 10.3 | 0.48 | 10.3 | 0.48 |
| First Midds Redust | 3.4 | 0.53 | 13.7 | 0.49 |
| First Break | 10.0 | 0.55 | 23.7 | 0.51 |
| Second Midds | 25.7 | 0.55 | 49.3 | 0.53 |
| Second Break | 8.3 | 0.59 | 57.6 | 0.55 |
| Grader | 3.6 | 0.60 | 61.2 | 0.55 |
| Third Midds | 6.4 | 0.91 | 67.6 | 0.58 |
| Third Break | 3.5 | 0.92 | 71.2 | 0.59 |
| Fourth Midds | 2.7 | 1.74 | 73.9 | 0.64 |
| Fifth Midds | 1.0 | 3.51 | 74.9 | 0.67 |
| Red Dog | 1.5 | 3.78 | 76.4 | 0.73 |

TABLE 1-continued

| Stream | Yield % | Ash % | Cumulative Yield % | Cumulative Ash % |
|---|---|---|---|---|
| Break Shorts | 4.2 | 4.47 | 80.6 | 0.93 |
| Reduction Shorts | 0.3 | 5.05 | 80.9 | 0.95 |
| Bran | 19.1 | 5.95 | 100.0 | 1.91 |

A 'straight grade' flour comprised of the first, second and third break streams, the first, second, third, fourth and fifth midds streams, the first midds redust and grader streams, and possessed a cumulative yield of 74.9% and a cumulative ash content of 0.67% on a dry weight basis with a starch damage level of 3.28%, and by comparison, a commercial pastry flour had a starch damage level of 4.07%, and a commercial durum semolina of 4.35%. The granulation of the soft durum flour being quite similar to that of the pastry flour (median particle size of 57 microns versus 47 microns, soft durum flour and pastry flour, respectively), and being markedly finer granulation than the durum semolina (median particle size of 400 microns).

In another exemplary embodiment, soft textured grain produced by a non-transgenic tetraploid wheat plant as disclosed herein (Soft Svevo), was milled on a modified Brabender Quadrumat Senior mill, wherein the first grinding head is a Quadrumat Junior head equipped with 2.8 inch diameter rolls possessing 18, 23, 25 and 30 corrugations, the second grinding head is the reduction head from a Quadrumat Senior equipped with 2.8 inch diameter rolls possessing 36, 36, and 41 corrugations, the last roll being smooth, both heads have been removed and are independent. The rolls operate on a 2.14 differential at 1200 and 560 rpm. The ground product from each head is collected and sifted on Great Western sifters using 12 inch diameter sieves, the first being clothed with U.S. No. 32 and 100 sieves, and sifted for 2 minutes, thus producing 'bran' (overs of No. 32), 'middlings' (the throughs of the No. 32 and overs of the No. 100), and break flour (the throughs of the No. 100); the middlings are then re-ground using the second head, the ground product of that grinding being sifted on the second sifter being clothed with a U.S. No. 100 sieve, for 3 minutes, the throughs are 'reduction flour' and overs are 'reduction shorts'. Break flour and reduction flour are combined to form 'straight grade' flour. The beginning grain weight is approximately 500 grams per milling. In common practice, soft wheat grain samples are tempered to 13% moisture content, and hard wheat grain samples to 14.5% moisture content. Durum wheats are commonly tempered to 16% (Posner and Hibbs, 1997, supra).

In this exemplary embodiment, three samples of Soft Svevo grain were tempered to 13.0, 14.5 and 16.0% moisture contents for 24 hr, and milled on the aforementioned modified Quadrumat Senior mill. The result of that milling was as follows: at 13% temper, 46.4% break flour yield, 21.8% bran yield and 70.7% straight grade flour yield with a 0.66% ash content; at 14.5% temper, 41.9% break flour yield, 27.2% bran yield and 66.2% straight grade flour yield with a 0.57% ash content; and at 16% temper, 38.2% break flour yield, 32.1% bran yield and 61.8% straight grade flour yield with a 0.55% ash content. These results being consistent with the endosperm and general kernel characteristics being as those of soft wheat, with an optimum temper level between 13 and 14.5%.

It is understood that the examples and embodiments described herein are for illustrative purposes only and that various modifications or changes in light thereof will be suggested to persons skilled in the art and are to be included within the spirit and purview of this application and scope of the appended claims.

What is claimed is:

1. A non-transgenic tetraploid wheat plant having grain with soft textured endosperm, or a part thereof, having all the physiological and morphological characteristics of the variety Soft Svevo Durum Wheat, WAS #080240001, representative seed of such line having been deposited with the American Type Culture Collection on May 29, 2009 and having been assigned ATCC accession No. PTA-10087.

2. The non-transgenic tetraploid wheat plant of claim 1, wherein the plant is capable of serving as a parent in a genetic cross.

3. A seed of the non-transgenic tetraploid wheat plant of claim 1, wherein the seed produces a non-transgenic teraploid wheat plant having grain with soft textured endosperm.

4. A tissue culture of regenerable cells produced from the plant of claim 1.

5. A protoplast produced from the tissue culture of claim 4.

6. A non-transgenic tetraploid wheat plant having grain with soft textured endosperm, regenerated from the tissue culture of claim 4.

7. A hybrid wheat plant, wherein the lineage of at least one parent plant comprises a non-transgenic tetraploid wheat plant having grain with soft textured endosperm, wherein the at least one parent plant has all the physiological and morphological characteristics of the variety Soft Svevo Durum Wheat, WAS #080240001, representative seed of such line having been deposited with the American Type Culture collection on May 29, 2009 and having been assigned ATCC accession No. PTA-10087.

8. The hybrid wheat plant of claim 7, wherein the at least one parent plant is the non-transgenic tetraploid wheat plant having grain with soft textured endosperm, with all the physiological and morphological characteristics of the variety Soft Svevo Durum Wheat, WAS #080240001, representative seed of such line having been deposited with the American Type Culture collection on May 29, 2009 and having been assigned ATCC accession No. PTA-10087.

9. A non-transgenic tetraploid wheat plant having grain with soft textured endosperm of the variety Soft Svevo Durum Wheat, WAS #080240001, representative seed of such line having been deposited with the American Type Culture collection on May 29, 2009 and having been assigned ATCC accession No. PTA-10087, or a selfed progeny thereof or an F1 hybrid thereof wherein the non-transgenic tetraploid wheat plant has grain with soft textured endosperm.

10. A flour milled from soft textured endosperm from a non-transgenic tetraploid wheat plant having grain with soft textured endosperm, wherein the non-transgenic tetraploid wheat plant is a non-transgenic tetraploid wheat plant known as Soft Svevo Durum Wheat, WAS #080240001, representative seed of such line having been deposited with the American Type Culture collection on May 29, 2009, and having been assigned ATCC accession No. PTA-10087 or a progeny thereof.

11. The flour of claim 10, wherein the flour has a low level of damaged starch.

12. The flour of claim 10, wherein the flour has a granulation similar to a pastry flour granulation.

13. The flour of claim 12, wherein the flour has a median particle size of about 57 microns.

14. The flour of claim 10, wherein the flour is a straight grade flour.

15. A semolina milled from soft textured endosperm from a non-transgenic tetraploid wheat plant having grain with soft textured endosperm, wherein the non-transgenic tetraploid wheat plant is a non-transgenic tetraploid wheat plant known as Soft Svevo Durum Wheat, WAS #080240001, representative seed of such line having been deposited with the American Type Culture collection on May 29, 2009, and having been assigned ATCC accession No. PTA-10087 or a progeny thereof.

16. The semolina of claim 15, wherein the semolina is used for making pasta.

17. Wheat grain kernels with soft textured endosperm, from a non-transgenic tetraploid wheat plant having grain with soft textured endosperm, wherein the non-transgenic tetraploid wheat plant with soft textured endosperm is a non-transgenic tetraploid wheat plant known as Soft Svevo Durum Wheat, WAS #080240001, representative seed of such line having been deposited with the American Type Culture collection on May 29, 2009, and having been assigned ATCC accession No. PTA-10087 or a progeny thereof.

18. Wheat grain kernels with soft textured endosperm, from a non-transgenic tetraploid wheat plant having grain with soft textured endosperm, wherein the non-transgenic tetraploid wheat plant with soft textured endosperm is a hybrid wheat plant, wherein the lineage of at least one parent plant of the hybrid wheat plant comprises a non-transgenic tetraploid wheat plant having grain with soft textured endosperm, wherein the at least one parent plant has all the physiological and morphological characteristics of the variety Soft Svevo Durum Wheat, WAS #080240001, representative seed of such line having been deposited with the American Type Culture collection on May 29, 2009 and having been assigned ATCC accession No. PTA-10087.

* * * * *